(12) United States Patent
Ishimaru et al.

(10) Patent No.: US 7,538,321 B2
(45) Date of Patent: May 26, 2009

(54) METHOD OF IDENTIFYING SUBSTANCES USING MASS SPECTROMETRY

(75) Inventors: Masako Ishimaru, Kokubunji (JP); Atsumu Hirabayashi, Kodaira (JP); Kinya Kobayashi, Hitachi (JP); Kisaburo Deguchi, Sapporo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 118 days.

(21) Appl. No.: 11/431,482

(22) Filed: May 11, 2006

(65) Prior Publication Data

US 2006/0255263 A1 Nov. 16, 2006

(30) Foreign Application Priority Data

May 13, 2005 (JP) ............................. 2005-141124

(51) Int. Cl.
H01J 49/00 (2006.01)
H01J 49/26 (2006.01)
H01J 49/40 (2006.01)

(52) U.S. Cl. .................... 250/288; 250/281; 250/282; 250/283; 422/67; 422/68.1; 702/27; 702/32

(58) Field of Classification Search ......... 250/281–283, 250/288; 422/68.1, 70, 67; 702/27, 32
See application file for complete search history.

(56) References Cited

U.S. PATENT DOCUMENTS 5,073,713 A * 12/1991 Smith et al. ................. 250/282
5,144,127 A * 9/1992 Williams et al. ............ 250/287
5,171,991 A * 12/1992 Johnson et al. ............. 250/292
5,206,509 A * 4/1993 McLuckey et al. ......... 250/292
5,572,025 A * 11/1996 Cotter et al. ................ 250/292

(Continued)

FOREIGN PATENT DOCUMENTS

JP 08-124519 5/1996

(Continued)

OTHER PUBLICATIONS

"Sequencing of Tri-and Tetraantennary N-Glycans Containing Sialic Acid by Negative Mode ESI QTOF Tandem M/S" by Sagi, et al. 2002 American Society for Mass Spectrometry. pp. 1138-1148.

(Continued)

Primary Examiner—Bernard E Souw
(74) Attorney, Agent, or Firm—Mattingly, Stanger, Malur & Brundidge, P.C.

(57) ABSTRACT

An object of the present invention is to provide a mass spectrometry system capable of improving an efficiency of obtaining information on a structure of substances, shortening a time taken for a measurement and substance identification, and improving identification accuracy. The system comprises: a process of mass analyzing an ionized analyte; a first fragmentation process where a first ion is selected from the ions observed in a mass spectrometry to fragment it; a process of mass analyzing a plurality of the ions generated in the first fragmentation process; a process of determining fragment ion combination capable of reconstructing the first ion using a result of the mass spectrometry; a second fragmentation process where the fragment ions contained in the fragment ion combination are fragmented; and a process of mass analyzing the fragment ions generated in the second fragmentation.

7 Claims, 17 Drawing Sheets

U.S. PATENT DOCUMENTS

| | | | |
|---|---|---|---|
| 5,696,376 A * | 12/1997 | Doroshenko et al. | 250/292 |
| 5,821,534 A * | 10/1998 | Park | 250/287 |
| 6,525,312 B1 * | 2/2003 | Cousins | 250/281 |
| 6,747,273 B2 * | 6/2004 | Brame et al. | 250/283 |
| 6,770,871 B1 * | 8/2004 | Wang et al. | 250/281 |
| 6,777,671 B2 * | 8/2004 | Doroshenko | 250/287 |
| 6,914,239 B2 | 7/2005 | Yoshinari et al. | |
| 6,917,037 B2 | 7/2005 | Ootake et al. | |
| 6,963,807 B2 * | 11/2005 | Townsend et al. | 702/27 |
| 6,987,261 B2 * | 1/2006 | Horning et al. | 250/282 |
| 7,157,698 B2 * | 1/2007 | Makarov et al. | 250/281 |
| 7,196,324 B2 * | 3/2007 | Verentchikov | 250/287 |
| 2002/0024010 A1 * | 2/2002 | Hager | 250/282 |
| 2003/0168589 A1 * | 9/2003 | Hager | 250/282 |
| 2004/0031918 A1 * | 2/2004 | Schoen et al. | 250/282 |
| 2005/0063864 A1 | 3/2005 | Sano et al. | |
| 2006/0255263 A1 * | 11/2006 | Ishimaru et al. | 250/288 |
| 2007/0278397 A1 * | 12/2007 | Bateman et al. | 250/286 |

FOREIGN PATENT DOCUMENTS

| | | |
|---|---|---|
| JP | 2004-257922 | 9/2004 |
| JP | 2005-091344 | 4/2005 |
| JP | 2005-241251 | 9/2005 |
| JP | 2005-345332 | 12/2005 |

OTHER PUBLICATIONS

Olsen et al., "Improved peptide identification in proteomics by two consecutive stages of mass spectrometric fragmentation," Proceedings of the National Academy of Sciences of the United States of America, Sep. 3, 2004, pp. 13417-13422.

* cited by examiner

FIG. 2
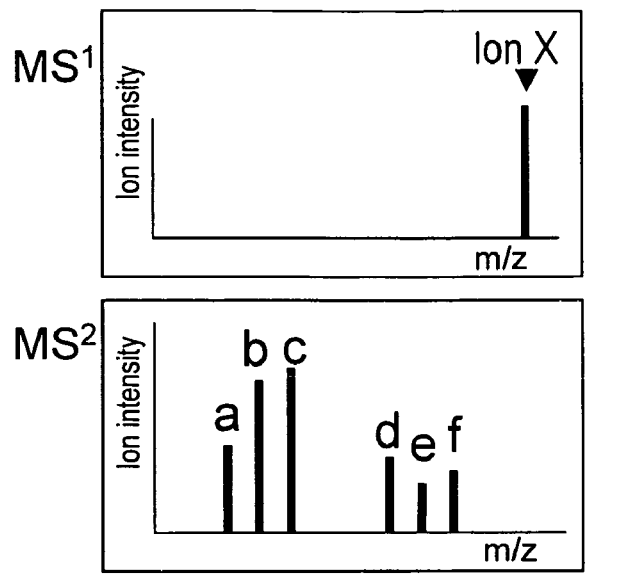
Legends  ○ Mannose
         □ N-acethylglucosamine
Ion X  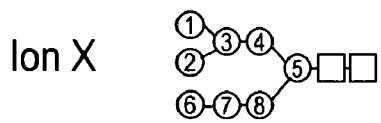
| a | ⑥-⑦ | |
| b | ①②-③ | ⑥-⑦-⑧ |
| c | ①②-③-④ | |
| d | ⑥-⑦-⑧-⑤□□ | |
| e | ①②-③-④-⑤□□ | ④-⑤□□ ⑥-⑦-⑧ |
| f | ①②-③-④-⑤□□ ⑧ | |

FIG. 3

Known protein No. 4
Known protein No. 3
Known protein No. 2
Known protein No. 1

Derivation: Bovine

Name of substance: Bovine Serum Albumin

Molecular weight: 69324 pI : 5.8

Amino acid sequence:  MKWVTFIS-- ---------- ----------

---------- ---------- ----------

:

---------- ---------- ----------

STQTALA

FIG. 13

```
Real time analysis  ☐ON    ☐OFF
    data base used                [      ]
    Oligosaccharide terminal modification [      ]
    Parent ion peak intensity threshold   MS2[      ]   MS3[      ]   MS4[      ]
    Retention time information in data base search    ☐Using  ☐Not using
        Retention time variation tolerance [      ]min
        Separation conditions [      ]
    m/z range of MSⁿ measurement parent ion
                        Include m/z  [      ] - [      ]
                        Exclude m/z  [      ] - [      ]
    User-specifying parent ion    m/z error    ± [      ]
```

| Retention time range (min) | m/z | z | include | exclude |
|---|---|---|---|---|
|  |  |  |  |  |
|  |  |  |  |  |
|  |  |  |  |  |
|  |  |  |  |  |

```
Spectrum matching       ☐ Yes  ☐ No
Fragment ion combination reading  ☐ Yes   ☐ No
    Number of combined fragments   ☐1   ☐2   ☐3   ☐4
    Storage of the read information    ☐ Yes  ☐ No
    MSⁿ of fragment ions               ☐ Yes  ☐ No
        Maximum value for n  [      ] (2~4)
Fragment reading to an unknown oligosaccharide, MSⁿ  ☐ Yes  ☐ No
MSⁿ repetition to a parent ion having a low ion intensity  ☐ Yes  ☐ No
    Parent ion peak intensity threshold  [      ]
    Number of repetition  ☐ Automatic  ☐ Specified  Maximum number [      ]
```

FIG. 14

Spectrum No. 4

Spectrum No. 3

Spectrum No. 2

Spectrum No.1

Title of measurement: test sample 1

Mode: +

Ion in-take time: 4 msec

CID energy: 6 n: 2

Parent ion: 1234.5(1+)

Spectrum

| m/z | Ion intensity I | z | m |
|---|---|---|---|
| 206.3 | 72.3 | | |
| 239.2 | 37.8 | | |
| 325.1 | 5.7 | | |
| 401.6 | 60.4 | | |

Spectrum matching

| Candidate oligosaccharide | Accuracy (%) |
|---|---|
| 210.1 | 67 |
| 200.1 | 53 |
| | |

Fragment combination reading

| Fragment ion combination | | Desorbed substance |
|---|---|---|
| 401.6 | 827.9 | $H_2O$ |
| | | |
| | | |

US 7,538,321 B2

METHOD OF IDENTIFYING SUBSTANCES USING MASS SPECTROMETRY

CLAIM OF PRIORITY

The present application claims priority from Japanese application JP 2005-141124 filed on May 13, 2005, the content of which is hereby incorporated by reference into this application.

BACKGROUND OF THE INVENTION

1. Field of the Invention

The present invention relates to a separation analysis system for analysis of an analyte containing many kinds of components. More particularly, this invention relates to a liquid chromatograph/mass spectrometry system, an analyzing method and equipment which are used for analysis of organism-related substances such as proteins, peptides, oligosaccharides, and metabolites.

2. Description of the Related Art

In recent years, a proteome analysis, a glycome analysis, and a metabolome analysis which allow comprehensive analysis of organism-related substances, such as proteins, oligosaccharides, metabolites which are contained in an organism texture and a body fluid, are being recognized to be effectively strategic mainly by those in the fields of biochemistry, innovative drug development, and food. For the analysis of them, the development of a high throughput analysis technology mainly using the mass spectrometry is emphasized.

In the mass spectrometry, a technology for high efficiently ionizing organism-derived molecules having high molecular weight has been advanced. The mass/charge ratio m/z of the ionized molecules can be measured using a mass spectrometer.

Molecules constructing an ion contain isotopes at a constant rate, whereby a series of ions containing isotopes is observed at the same time. The interval on the m/z axis is 1/z so that the charge of an ion can be judged. The mass m of an ion is calculated from the m/z and z values. Furthermore, the use of an ion trap method allows one of ions observed in the first-time mass spectrum (hereinafter referred to as $MS^1$) to be selectively left. This ion serves as a parent ion to be fragmented using a CID (Collision Induced Dissociation), an IRMPD (InfraRed MultiPhoton Dissociation), or an ECD (Electron Capture Dissociation), whereby the spectrum of the fragment ion can be obtained (hereinafter referred to as $MS^2$; fragment ion is also called a product ion). One of the obtained fragments can further be fragmented ($MS^3$, $MS^4$ and so on; hereinafter, a measurement is described as $MS^n$, where $n \geq 2$). The sort of a fragmenting method and a fragmenting energy can be controlled to dissociate the particular kind of the intramolecular binding during the process of fragmentation. Information on the molecular structure of the parent ion can be obtained from the fragment ion resulted from fragmentation. When information is insufficient, continuation of the $MS^n$ measurements provides further information.

For example, in the analysis of the peptide which is a polymer of several tens of molecules of amino acids, fragmentation is performed such as to break the binding between amino acids, and the fragments having a difference in mass that matches the mass of one of the twenty kinds of amino acids are sequentially found from many kinds of fragments generated by the breaking of any binding, whereby an amino acid sequence of the peptide can be read sequentially from the edge. At this time, the information for identifying substances can be efficiently obtained by automatically reading the amino acid sequence from the peptide fragments observed in the spectrum before the obtaining of the next spectrum to select the most appropriate ion as a parent ion for the next fragmentation. This method can be said to be particularly useful technology when carrying out LC/MS (liquid chromatography/mass spectrometry) measurement because the time width in which a certain component is eluted from an LC is limited (refer to Japanese Unexamined Application Publication No. 2004-257922).

For example, in the analysis of oligosaccharide, fragmentation is performed such as to break the binding between monosaccharides or the cyclic structure of the monosaccharide to observe a fragment specific to a certain oligosaccharide, the structural information of which has been registered in a data base (hereinafter described as "known"), whereby the oligosaccharide to be analyzed can be identified in some cases (refer to Journal of the American Society for Mass Spectrometry (2002) p. 1138-1148).

A sugar includes many stereo isomers having the same mass. There also exist two kinds $\alpha$ and $\beta$ of cyclization forms sterically different from each other. Furthermore, the oligosaccharide which is formed by chain polymerization of monosaccharides also includes ones having a branched structure. The oligosaccharides which have the same mass but have many different structures are therefore likely to be available. Therefore, it is difficult to uniquely determine the structure of the oligosaccharide, the structural information of which has not been registered in the data base (hereinafter described as "unknown"), by means of the mass spectrometry.

Therefore, with respect to multiple kinds of known substances, the mass spectra of the fragments obtained under certain ionization and fragmentation conditions are previously prepared, and the analyte is then measured under the same conditions as above to obtain a mass spectrum. A spectrum matching technique where the obtained spectrum pattern is compared with that of the previously prepared spectrum can subsequently be performed to judge whether the analyte is the same as a known substance.

The data base of the substances which tend to desorb during fragmentation is previously established. Then, the data base is searched to determine the attribution of fragment ion, whereby the candidate of a parent ion can be determined by finding the combination of the fragment ion with a desorbed substance (refer to Japanese Unexamined Application Publication No. Hei8-124519).

SUMMARY OF THE INVENTION

To fragment an ion for the purpose of obtaining further information on a molecular structure, an $MS^n$ measurement that further fragments one of the fragmented ions can be performed. The parent ion which is to be next fragmented has so far been selected in order of ion intensity starting from the strongest ion when a plurality of fragment ions are simultaneously observed. The intensity of the ions observed in the obtained spectrum decreases as fragmentation continuously proceeds in the order of $MS^2$, $MS^3$ and so on. Therefore, it is advantageous from the point of view of sensitivity to select a stronger ion as a parent ion For example, in the pages of 13417 to 13422 of Proceedings of the National Academy of Science of the United States of America (2004), $MS^2$ measurement is performed on peptide ions and three of the multiple observed fragment ions are selected as parent ions to perform $MS^3$ measurements. If a fragment containing a C-terminal of the peptide and a fragment containing an N-terminal are included in three strong fragment ions by chance, most of the peptide sequence can be read to identify the peptide.

However, a problem occurs when, among observed fragmented ions, a series of fragmented ions containing one end has a high ion intensity, while another series of fragmented ions containing the other end has a low ion intensity. The problem is that this results in the selection of only fragmented ions to which one end belongs, as the parent ion which is to be next fragmented, and the information on the molecular structure of the other end is not obtained. When a data analysis performed after obtaining data reveals that the information on the other end lacks at the time when the assignment of each ion observed is tried, remeasurement must be performed so that time is wasted.

When using a separating means such as a liquid chromatography (LC) and an electrophoresis as a procedure previous to the mass spectrometry, a mixture comprising a plurality of substances is separated into each substance by a separation column. Each substance separated is individually eluted in different time periods and ionized on-line by use of ionizing means to be introduced into a mass spectrometer. In view of one of a plurality of the substances, the time period allowed to introduce this substance is limited to the peak width of a separation band. Taking into consideration that, to obtain one spectrum, a mass spectrometer requires a certain time or more that depends on the performance of the equipment, it is understood that there is an upper limit of the number of times to perform $MS^n$ measurements. For example, when the peak width of the separation band of substance A is five seconds and when the mass spectrometer requires one second to obtain one spectrum, the upper limit of the number of times of $MS^n$ measurements on substance A is five. It is assumed that the first measurement of five measurements is done as $MS^1$, the second measurement is performed as $MS^2$ on the strongest ion of the ions observed in the $MS^1$, and the third to fifth measurements are performed as $MS^3$ on each of three ions of fragment ions observed in the $MS^2$ as a parent ion. It is here assumed that the three fragment ions selected as parent ions of the $MS^3$ individually amount to (1) 20%, (2) 30%, and (3) 50% of the mass of the substance A. When there is no molecular structural duplication between three ions, information on 20+30+50=100% of the molecular structure of the substance A is obtained through $MS^3$ measurement. On the other hand, when the molecular structures of the (1) and (2) ions respectively are contained in the molecular structure of the (3) ion, $MS^3$ measurement only provides information on 50% of the molecular structure of the substance A. Thus, when biased information on the molecular structure obtained through $MS^n$ measurements is provided for one substance, the information obtained is likely to be not enough to achieve identification.

The corrective actions to this problem taken on a conventional $LC/MS^n$ automatic measurement equipment includes an action having a function of selecting one ion less than a certain number of times as the parent ion for $MS^2$ measurement, and an action having a function of specifying the m/z of an ion which is selected or not selected as a parent ion prior to a measurement. However, the parent ion for $MS^n$ measurement is actually automatically selected in order of intensity starting from the highest intensity, and actions used to obtain information on an entire molecular structure are not taken.

It is an object of the present invention to provide a mass spectrometry system which improves the efficiency of obtaining information on the structure of substances, shortens the time for measurement and substance identification, and improves the identification accuracy.

To meet the purpose above, the present invention introduces a mechanism of selecting an appropriate ion as a parent ion for the next $MS^n$ measurement by analyzing data every time one spectrum is measured to improve efficiency of obtaining information on a molecular structure.

A mass spectrometry system according to the present invention comprises a mass spectrometer which mass-analyzes an ionized analyte, and an information processing section. The mass spectrometer has a function of selectively fragmenting an ion having a particular m/z appearing on a mass spectrum and then mass-analyzing the fragmented ion. The information processing section has a fragment ion combination reading processing section which receives information on a parent ion and a plurality of the product ions derived from the parent ion to determine the combination of product ions that allows reconstruction of the parent ion, and has a function of directing the mass spectrometer to fragment the product ions included in the combination of product ions determined by the fragment-ion combination reading processing section, and to perform mass analysis.

The fragment ion combination reading processing section determines the combination of product ions that meet the following equation (1).

$$m = m_1 + m_2 + \ldots + m_s + A \text{ (s is a positive integer not less than 2 and less n)} \quad (1),$$

where:
m is the mass of the parent ion;
$m_1, m_2, \ldots,$ and $m_n$ (n is a positive integer not less than 2) are the mass of the product ions; and
A is the mass of a molecule desorbed during fragmentation of the parent ion.

The mass spectrometry according to the present invention comprises: a process of ionizing an analyte; a process of mass-analyzing the ionized analyte; a first fragmentation process where a first ion selected from ions observed in the mass spectrometry is fragmented; a process of mass-analyzing a plurality of the ions generated in the first fragmentation process; a process of determining the combination of fragment ions that allows reconstruction of the first ion using the result of mass-analysis; a second fragmentation process where a fragment ion contained in the combination of the fragment ions is fragmented; and a process of mass-analyzing the fragment ions generated in the second fragmentation process.

Also, the present invention provides a program which makes a computer execute the process of determining a combination of product ions that allows reconstruction of the parent ion by receiving information on the parent ion and the plurality of the product ions generated through the fragmentation of the parent ion from the mass spectrometer, and the process of directing the mass spectrometer to perform mass analysis by fragmenting the product ions contained in the determined combination of the product ions. In this program, a combination of the fragment ions which meets the equation (1) above is determined through the process of determining the combination of the product ions that allows reconstruction of the parent ion.

The present invention improves the efficiency of obtaining information on the structure of a substance, shortens the time taken for measurement and identification of the substance, and improves identification accuracy in identification of the substances by means of mass spectrometry.

BRIEF DESCRIPTION OF THE DRAWINGS

FIG. 2 is a schematic view showing a method where suitable fragments are observed in an $MS^2$ measurement to perform fragment ion combination reading processing with respect to a typical oligosaccharide.

FIG. 3 is a schematic view showing an example of a data sheet of a protein stored in a known protein data base.

FIG. 13 is a schematic view showing a user parameter input display in a mass spectrometer having a function of performing a real time analysis.

FIG. 14 is a schematic view showing an example of data to be stored in a measurement data storage section, after a real time spectrum matching and fragment combination reading processing.

DETAILED DESCRIPTION OF THE PREFERRED EMBODIMENTS

Figure 1:
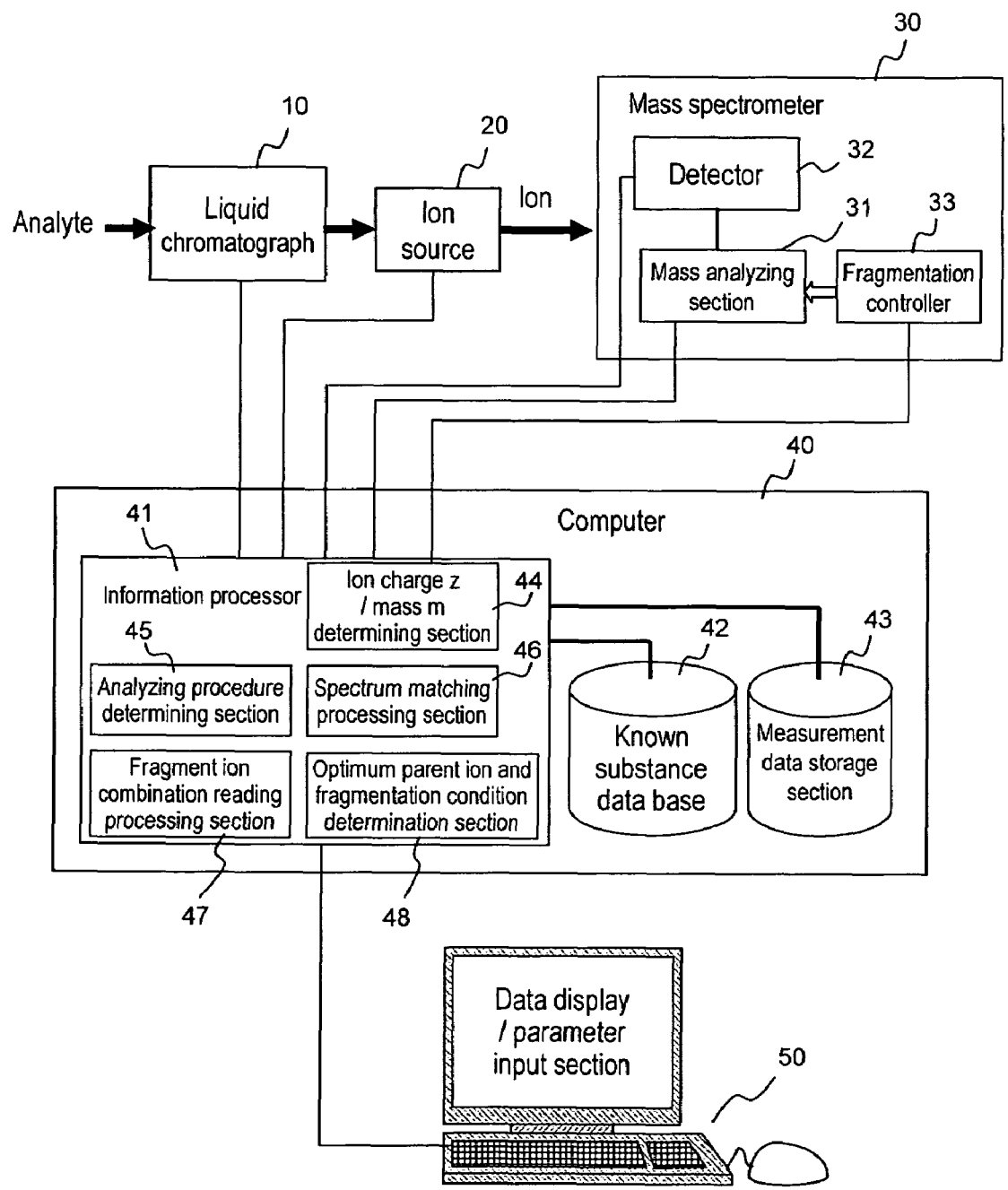
FIG. 1 is a block diagram showing the equipment configuration of a spectrometry system according to the present invention.

FIG. 1 shows an example of equipment configuration of a mass spectrometry system according to the present invention. FIG. 1 shows an example of the configuration of the mass spectrometry system which analyzes in real time a spectrum data obtained through $LC/MS^n$ measurements, which comprises a liquid chromatograph 10, an ion source 20, a mass spectrometer 30, a computer 40, and a data display and parameter input section 50.

A mixture of multiple substances which is an analyte is introduced into the liquid chromatograph 10. A separation column which separates substances depending on the properties thereof is mounted to the liquid chromatograph 10. The analyte which has passed through the separation column is separated into components, each of which is eluted after different elapses of time. Each eluted component of the analyte is ionized by the ion source 20. The ions are introduced into the mass spectrometer 30. The spectrometer 30 comprises a mass analyzer 31, a mass spectrum detector 32, and a fragmentation controller 33. The mass spectrum detector 32 obtains the mass spectrum of the introduced ions. The fragmentation controller 33 controls the conditions under which ions are fragmented. The mass spectrum is transferred to an information processor 41 in the computer 40. The computer 40 comprises an information processor 41, a known substance data base storage section 42 which stores the $MS^n$ (n=1, 2, 3, . . . ) spectrum data of known substances, and a measurement data storage section 43. The information processor 41 comprises an ion charge z/mass m determination section 44, an analyzing procedure determination section 45, a spectrum matching processor 46, a fragment ion combination reading processor 47, and an optimum parent ion and fragmentation condition determination section 48. The information processor 41 checks the obtained spectrum of an ion against the data of known substances, and, when identification is not achieved, determines the conditions under which the next mass spectrum is obtained to obtain further data on the ion. The fragment ion combination reading processor 47 reads the combination of the fragment ions that constructs the entire original parent ion from the ions observed in the spectrum ($MS^n$ spectrum, $n \geq 2$) obtained by selecting an ion as a parent ion and fragmenting it.

This system configuration allows the spectrum data to be analyzed in real time to sequentially determine the conditions for the next measurement in the $LC/MS^n$ measurement so as to make it possible to efficiently obtain a spectrum.

FIG. 2 shows an example of the real time analysis of the $MS^n$ spectrum of a typical oligosaccharide according to the present invention An analyte represents the oligosaccharide which is composed of eight mannoses and two N-acetylglucosamines and has a branched structure as an example of various kinds of oligosaccharides. Each mannose is given one of the numbers from 1 to 8 to be represented.

The spectrum which is obtained when this oligosaccharide is fragmented as a parent ion is shown in FIG. 2. One or more bindings of the parent ion in a molecule are likely to be simultaneously broken. The present embodiment shows the $MS^2$ spectrum generated when only one binding of the original oligosaccharide is broken. The fragments formed by breaking 3-4, 4-5, 7-8, and 5-8 bindings of the bindings between monnoses are observed in a spectrum. The assignments of each peak are shown in a to f.

When the structure of the substance is unknown and further information on the structure is necessary, an $MS^3$ spectrum can be obtained by further fragmenting some of the fragments.

Assuming that a fragment combination reading according to the present invention is performed in selecting a parent ion for fragmentation. Breaking a binding of the original oligosaccharide produces two fragments. By a reading performed with the setting of a two-fragment combination reading, peak combinations a and f, b and e, and c and d are detected as a combination of fragments generated by breaking a binding of the parent ion. Any selection of these combinations as a parent ion of $MS^3$ provides the information on the entire structure of the molecule. For example, if the priority is assigned to these combinations in order of decreasing sum of ion intensities of two fragments, the priority is in order of the peaks c and d, b and e, and a and f. This order leads to the first $MS^3$ fragmentation of the peak c and the second $MS^3$ fragmentation of the peak d, and $MS^3$ spectra at both non-reducing terminal and reducing terminal of oligosaccharide are consequently obtained.

On the contrary to this, if a parent ion is selected according to the prior art in order of decreasing ion intensity, the priority is in order of the peak c, b, a, d, e, and f. Any of the peaks c, b, and a is an oligosaccharide fragment at the non-reducing terminal. This results in the fact that information on the reducing terminal cannot be obtained until the forth $MS^3$.

When the fragment ion combination reading processing is performed as described above, information on a molecular structure can efficiently be obtained.

The known substance data base 42 of the present invention includes a data base of organism substance such as protein, oligosaccharide, lipid, and nucleic acid, and a data base of artificially synthesized substance. An example of the data base of the known substances of protein, and oligosaccharide is hereinafter described.

FIG. 3 shows a protein data base which includes information including origin of protein, name, molecular weight, isoelectric point, amino acid sequence as an example of the data base for the analysis of protein. The base sequence of genes which is stored in the gene data base which is disclosed on a worldwide web, and the translation of the gene sequence determined by a user can also be used as the amino acid sequence of protein. The list of peptides which is formed by enzymatic-digestion protein is prepared by means of a calculator using the amino acid sequence of protein. Furthermore, the list of fragments which are formed by fragmenting each listed peptide using a mass spectrometer is prepared. This fragment list can be considered as the $MS^n$ spectrum of known substances.

Figure 4:
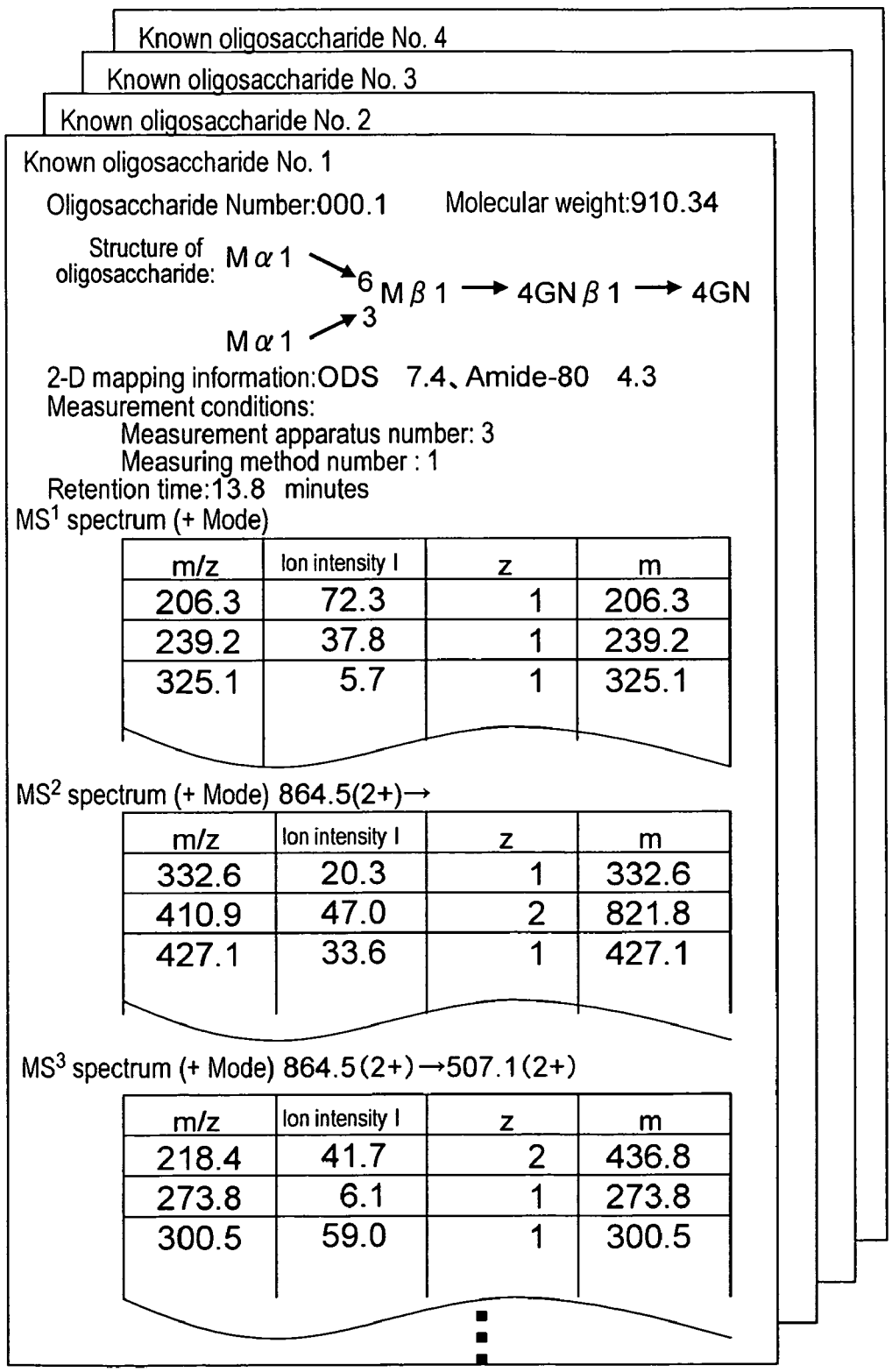
FIG. 4 is a schematic view showing an example of a data sheet of an oligosaccharide stored in a known oligosaccharide data base.

FIG. 4 shows an oligosaccharide data base including information such as the symbol showing the kind of oligosaccharide, the molecular weight, the structure and mass spectrum of oligosaccharide as an example of the data base for the analysis of oligosaccharide. When the structure of oligosaccharide is unknown, a description "unknown" is made. When the position of oligosaccharide in a two-dimensional oligosaccharide map is known, this information may be included in the data base. When the oligosaccharide mass spectrometry data base generally disclosed is available, this can be used. Alternatively, a user is capable of previously mass-analyzing some oligosaccharides to register the obtained information. The spectra of $MS^1$, $MS^2$, $MS^3$, $MS^4$, . . . are registered as a mass spectrometry data of oligosaccharide. There is no upper limit of n value of $MS^n$, which typically is about 20 or less. The equipment used to obtain these spectra, and the title of the method file in which measuring conditions are stored are simultaneously recorded. A measuring mode (+or −), and the information on the parent ion are attached to each $MS^n$ spectrum. Moreover, a user is capable of previously performing LC/MS analysis for some oligosaccharide to attach the information on a retention time.

For a certain analyte to be measured, variations of a fragmenting energy and methods, for example, CID and ECD, can be considered. Furthermore, ion trap, time-of-flight, and magnetic sector methods are available as a method of mass spectrometry. Therefore, the method of mass spectrometry can be considered to be changed to perform measurement. Hereinafter is described an example of the method which makes the known substance data base usable even when the measuring conditions to perform a measurement is changed.

Case 1. Measuring Under Certain Fixed Fragmenting Conditions

The known substance data base stores a spectrum obtained when the fragmenting of the known substance is performed under fixed fragmenting conditions. The information which can be stored on each known substance includes the m/z, and m and z values of the parent ion, and the m/z, m and z values, and ion intensity of the product ion which appears on $MS^n$ (n=2, 3, . . . ) spectrum. Whenever knowledge has been obtained about the separation by means of the LC, the information on the kind of the separation column, the kind of the solvent, and retention time may be included.

Case 2. Measuring Under Variable Fragmenting Conditions

The known substance data base stores the m/z, and m and z values of the parent ion, and the m/z, m and z values, and ion intensity of the product ion obtained under each fragmenting conditions in addition to the information stored in the above case 1 where a measuring is performed under fixed fragmenting conditions Case 3. Measuring Using Measuring Equipment Different in Fragmenting Method and in Spectrum Obtaining Method It is impossible to obtain the $MS^n$ spectra of all known substances under all fragmenting conditions. Furthermore, a spectrum obtained by certain measuring equipment is not always obtainable by other equipment of different measuring methods, because the manner of fragmenting an ion and the obtained $MS^n$ spectrum differ depending upon the methods (ionizing method, fragmenting method, mass analyzing method, and the like) employed by the measuring equipment.

The following method is then devised as a method making applicable a known substance data base which stores information on a spectrum obtained by certain measuring equipment employing a method, to a spectrum obtained by other measuring equipment employing a different method. First, a plurality of typical standard substances are determined. These standard substances are measured by measuring equipment which employs another method under a plurality of fragmenting conditions to obtain $MS^n$ spectrum data. This $MS^n$ spectrum data is compared with the $MS^m$ spectrum data of the same substance stored in the known substance data base. At this time, n is not necessarily the same as m. Thus, a function is determined, which is used to convert the $MS^n$ spectrum data stored in the known substance data base to the $MS^n$ spectrum data obtained by measuring equipment which employs another method. After that, when reference is made to the known substance data base, the spectrum converted by this function is applied.

The above system which has the known substance data base allows an ensured spectrum matching processing, thereby resulting in correct judgment whether the subsequent fragment reading is proceeded or not.

Figure 5:
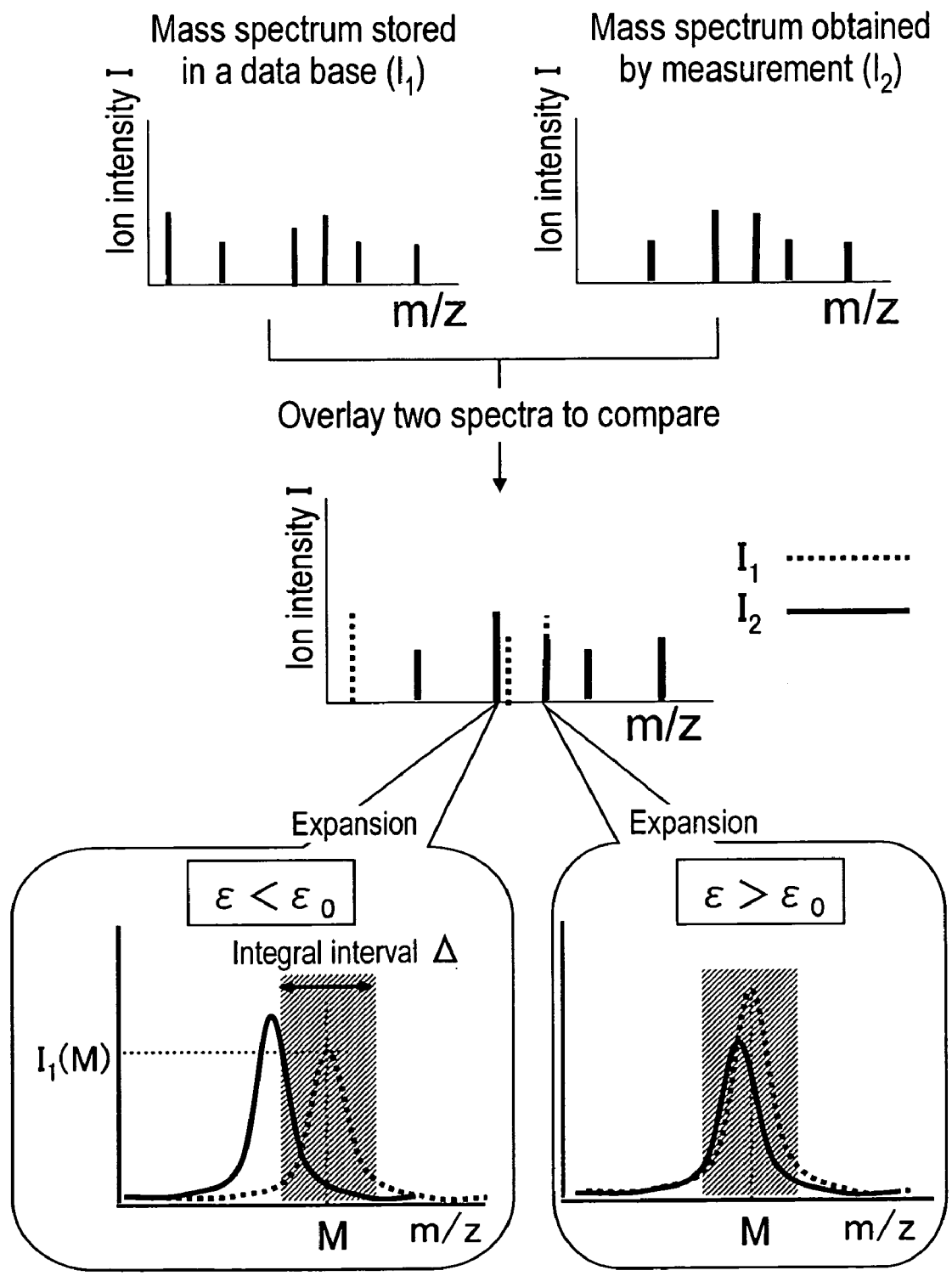
FIG. 5 is a schematic view illustrating a method of mass spectrum matching between two spectra.

There is a spectrum matching method as a method for identifying a substance by comparing the mass spectrometry spectrum obtained through an actual measurement with the information on the mass spectrometry spectrum of the known substance stored in the known substance data base. FIG. 5 shows an example of the spectrum matching method.

Assume that the mass spectrum obtained through a measurement is compared with one of the spectra stored in the data base to judge a coincidence between them. At this time, comparison may be made between each of all spectra stored in the data base. When information on the mass spectrum obtained through a measurement such as a retention time in the LC, and the origin of the analyte to be measured, is known, the processing time can be shortened, by previously limiting the data to be compared amongst the data stored in the data base, and by reducing the number of times a spectrum matching is performed.

As shown in FIG. 5, the mass spectra obtained through a measurement is superposed with one of the spectra stored in the data base to calculate the value corresponding to the coincidence between them from the value of the ion intensity I of the peak with respect to all peaks in the spectrum. If the value amounts to a certain value or more, or amounts to a certain value or less, two spectra are judged to be the same. An example of the method for calculating a coincidence is described below. An $\epsilon$ value is calculated using the equation (2) below.

$$\varepsilon = \frac{\int_{-\Delta/2}^{\Delta/2} \{I_1(M+\delta) \cdot I_2(M+\delta)\} d\delta}{I_1(M)^2} \quad (2)$$

where:

$\Delta$ is the accuracy of the m/z of the measuring equipment;

$I_1$ (m) is the ion intensity of the ion having mass m in the mass spectrum stored in the data base;

M is the m/z value of the peak in the mass spectrum stored in the data base; and $I_2$ (m) is the ion intensity of the ion having mass m in the mass spectrum obtained through an actual measurement.

The $\epsilon$ value expresses the extent of superposing between two peaks. The larger the value, the higher the coincidence is. The $\epsilon$ value is calculated with respect to all peaks. For example, if the $\epsilon$ value amounts to larger than a certain value $\epsilon_0$ with respect to all peaks, it is judged that two spectra coincide with each other. The value $\epsilon_0$ can be determined by a user from the measuring accuracy of the equipment and the result of the measurement of the standard substances.

No further analysis is judged to be needed to be performed with respect to an ion which is identified to be a known substance through this operation. And thereby, the analyzing time can be shortened.

Figure 6:
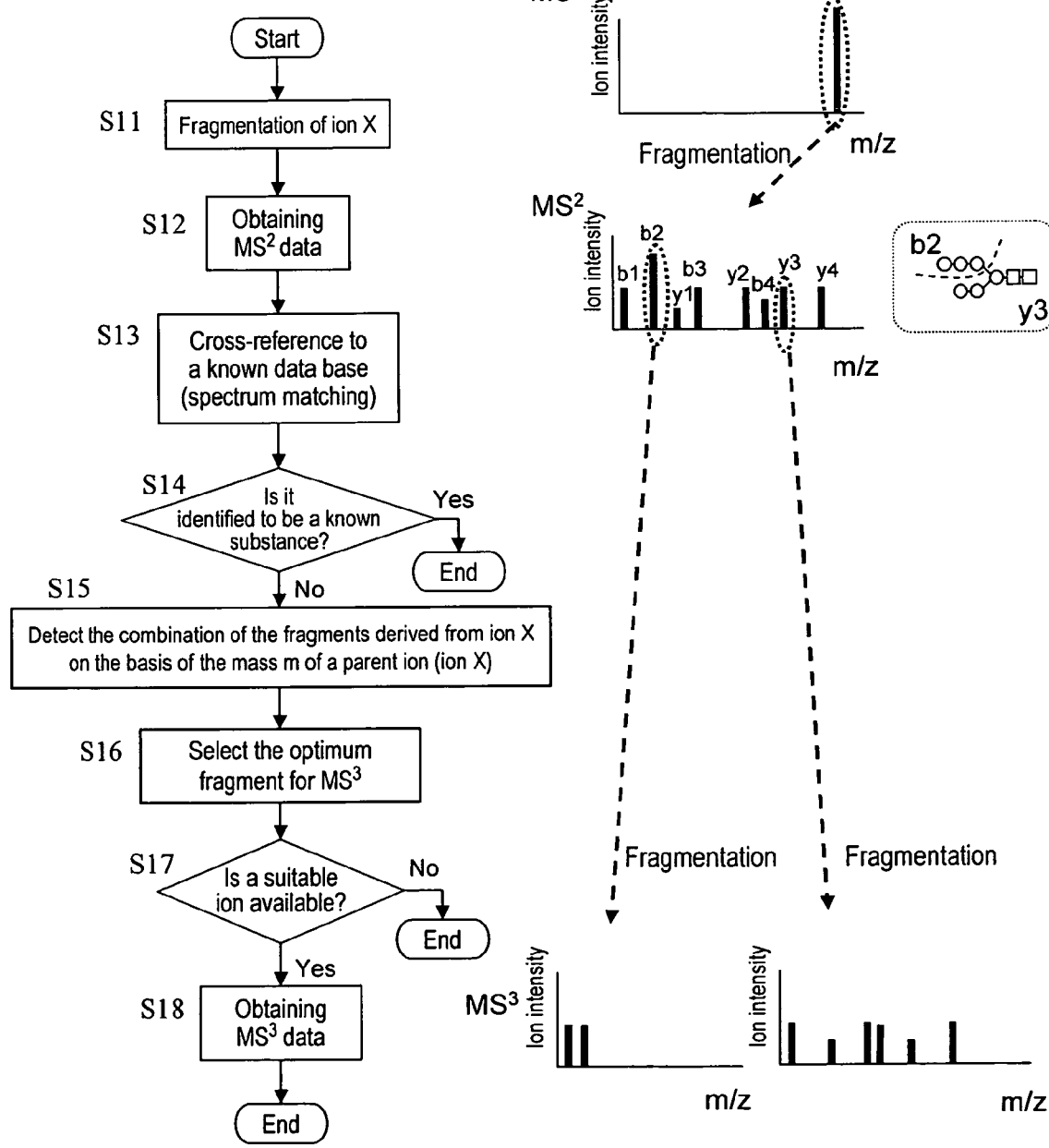
FIG. 6 is a flow diagram showing an analysis procedure of a real time identification of substances.

FIG. 6 shows an example of procedures of a real time analysis. The mass spectrometry system of the present invention shown in FIG. 1 performs an analysis following the procedure below.

An ion X having a certain m/z is subjected to an $MS^2$ measurement (S11). When, during fragmentation, just a neutral loss occurs and fragments formed by breaking the intramolecular bindings are not obtained, a further fragmentation is necessary. In this example, however, it is assumed that the $MS^2$ measurement not only indicates a neutral loss but also provides fragments formed by the dissociation of the intramolecular binding. A mass spectrum is obtained in the mass spectrum detector 32 to calculate the z and the m from the m/z value of the parent ion and the interval between peaks of the isotopes in the ion charge z/mass m determining section 44 (S12).

In separation by means of the liquid chromatography prior to a mass spectrometry, known candidate substances are narrowed down according to the information on the retention time. A known substance ion which has the same m value as that of the analyte is then searched in the known substance data base 42 in the spectrum matching processor 46. Subsequently, a spectrum matching process is performed between the $MS^n$ spectrum of the known substance ion and the $MS^2$ spectrum of the ion which has actually been measured (S13). The data base 42 stores the $MS^n$ (n=1, 2, 3, ...) spectrum data with respect to the known substances. The spectrum matching process is performed between all these spectrum data and the actually measured $MS^2$ spectrum. When the spectrum matching process identifies the parent ion to be a known substance, the analyzing procedure is terminated with respect to this parent ion (S14, Yes).

Figure 7:
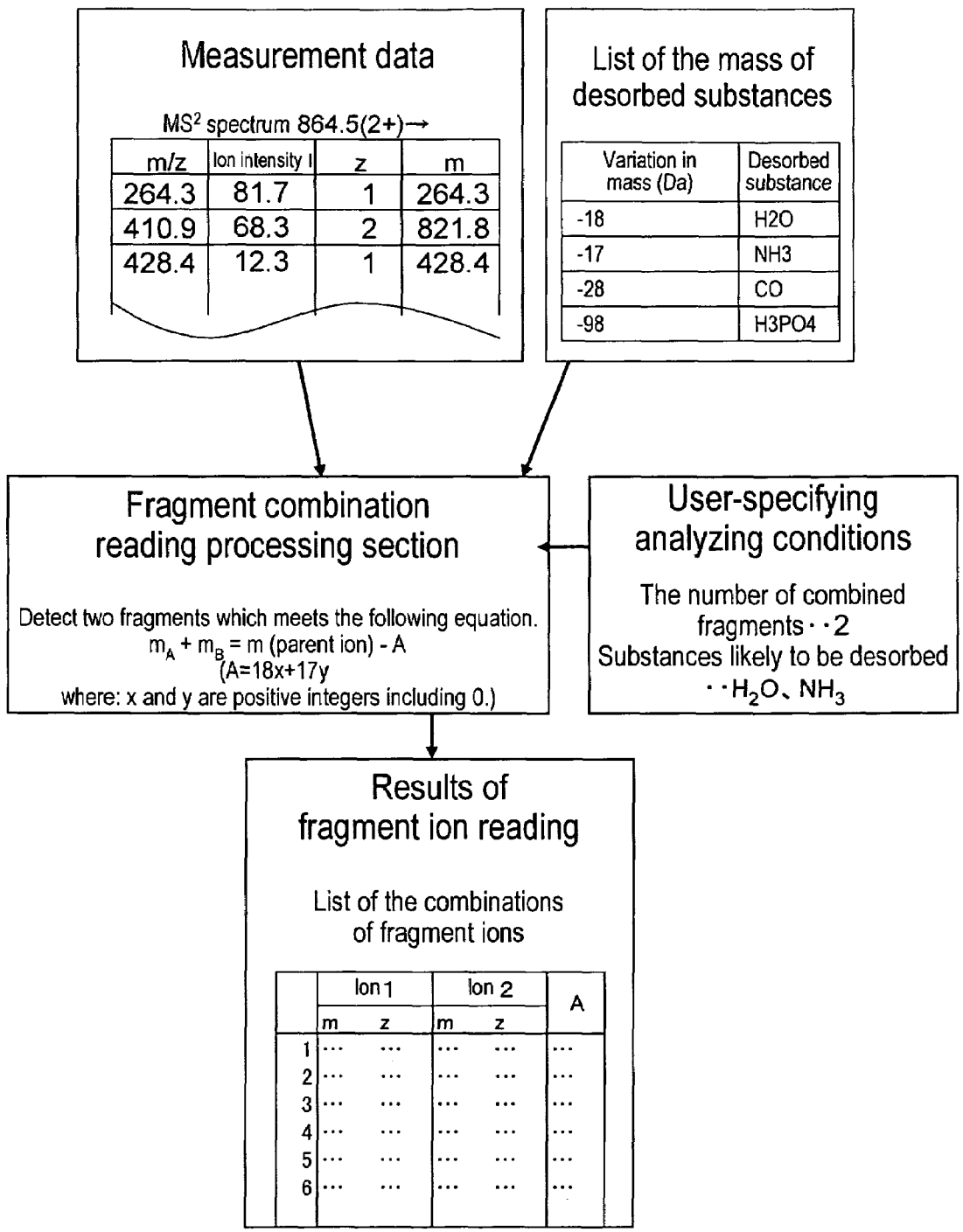
FIG. 7 shows a schematic view showing a procedure of processing fragment combination reading.

When the spectrum matching process doesn't judge the parent ion to be a known substance (S14, No), the combination of the fragments derived from the parent ion is detected on the basis of the m of the parent ion(S15). Two or more of the numbers of the fragments to be combined can optionally be specified by a user. FIG. 7 herein shows an example of a fragment ion reading procedure used when 2 is specified as the numbers of the fragments to be combined. This process is executed in the fragment ion combination reading processor 47. The combination of $m_a$ and $m_b$ that meets the following equation (3) is detected.

$$m = m_a + m_b \quad (3)$$

where $m_a$ and $m_b$ each is the mass of the two of the fragment ions observed in the $MS^2$ spectrum obtained through the measurement.

When $H_2O$ or the like is simultaneously desorbed during the dissociation of the binding, two ions which meet the following equation (4) are to be found taking the above condition into consideration.

$$m = m_a + m_b + A \quad (4)$$

where A is the total mass of the desorbed substance.

The substances shown in a list of the masses of the desorbed substances in FIG. 7 are an example of the substances known to be desorbed during the fragmentation of peptide. In the present embodiment, the value corresponding to A in the above equation is calculated using these masses. When an analyte peptide is known not to have been phosphorylated, the desorption of phosphoric acid may previously be excluded from options, whereby the accuracy of the combination reading processing is improved. If other substances which are possible to be desorbed are also known not to be desorbed in the measurement, desorption of these substances may be excluded from the options, whereby the accuracy of the combination reading processing is improved. The embodiment shown in FIG. 7 describes the fragment ion combination reading process that is to be performed under the conditions that $H_2O$ and $NH_3$ are specified as substances likely to be desorbed. Thus, the data base of desorbed substances is simultaneously available. The reference to this data base during detection of a combination allows the improvement in reliability of the detected combination.

Referring back to FIG. 6, an optimum parent ion and fragmentation condition determining section 48 gives the detected combinations priorities in order of decreasing suitability as a parent ion for the $MS^{n+1}$ measurement (S16). The examples of priority assigning criteria includes an ion intensity of a fragment peak, and an ion charge z of a fragment. The higher the ion intensity of a parent ion is, the higher the peak intensity of the $MS^{n+1}$ becomes, and the easier the analysis becomes. Also, a bivalent parent ion is more efficiently fragmented than a univalent parent ion. Therefore, a method is considered in which the ion combinations are given priorities as a parent ion for the $MS^{n+1}$ measurement in order of decreasing intensity of peaks and further decreasing number of bivalent ions contained in the combination. The optimum parent ion and fragmenting condition determining section 48 determines dissociation conditions such as the CID, under which suitable fragments can be obtained from the fragments contained in combinations selected as the parent ion for the $MS^{n+1}$ measurement. The information processor 41 sets dissociation conditions to the fragmenting controller 33 of the mass spectrometer 30 to perform the $MS^{n+1}$ measurement (S18). When no suitable combination is available, the analyzing procedure is terminated (S17, No) with respect to ion X.

The analyzing procedure above makes it possible to efficiently perform a matching between the observed ion and the known substance, a judgment whether it is necessary to obtain further data or not, and a selection of a parent ion for obtaining further data.

Figure 8:
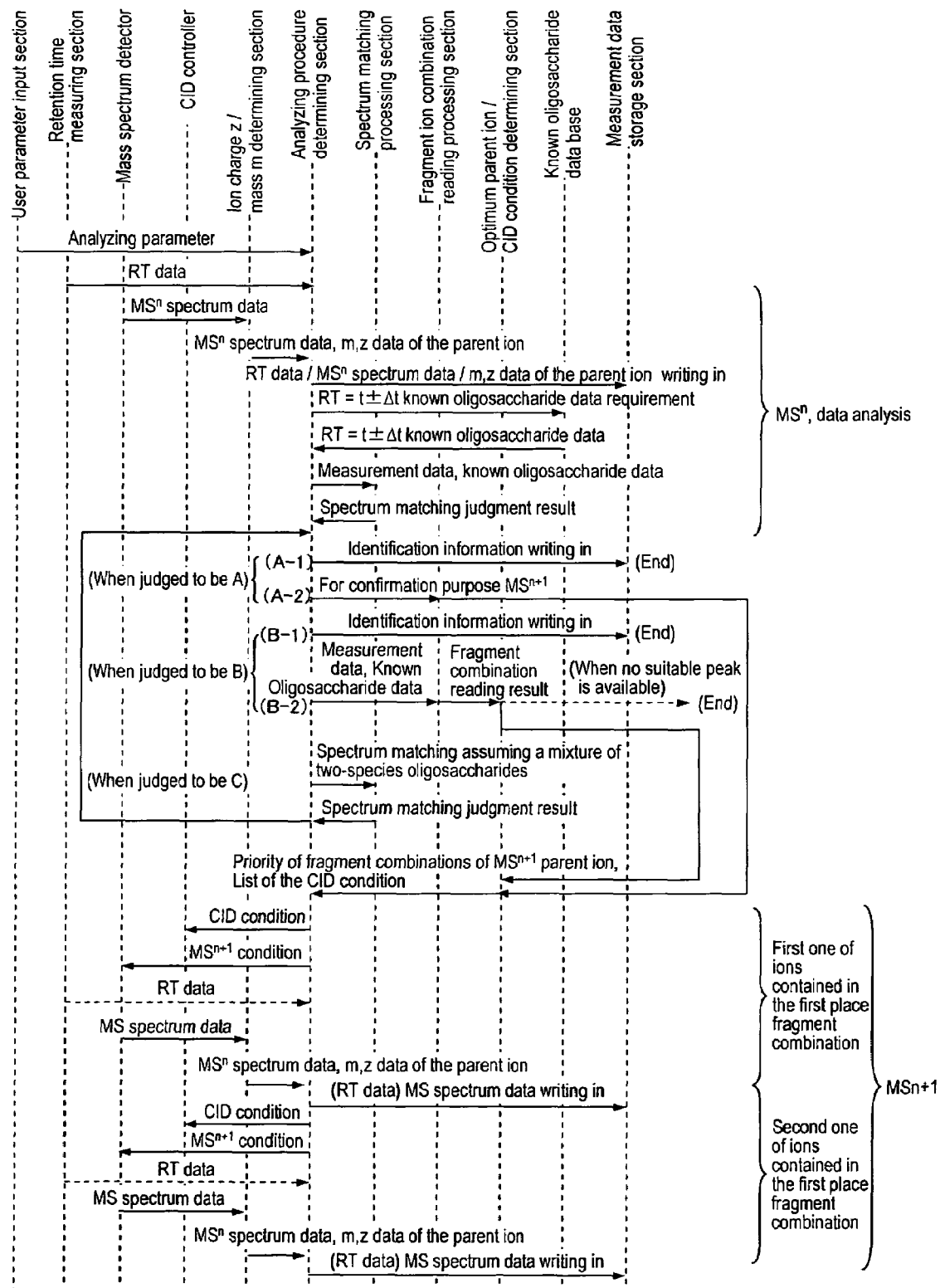
FIG. 8 is a flow diagram showing flows of information between each section of mass spectrometry system.

FIG. 8 shows an example of the information that flows between sections in a mass spectrometry data processing system assuming that the analysis of oligosaccharide is performed according to the present invention.

As shown in FIG. 1, the mass spectrometry data processing system comprises: a user parameter input section 50; a mass spectrum detector 32; CID controller (fragmentation controller 33); an ion charge z/mass m determining section 44; an analyzing procedure determining section 45; a spectrum matching processor 46; a fragment ion combination reading processor 47; an optimum parent ion/CID condition determining section 48; a known oligosaccharide data base storing section 42; and a measurement data storage section 43. The system also includes a retention time measuring section when the liquid or gaseous analyte separated by the liquid chromatograph 10 is introduced online into the mass spectrometer 30. The information flow in the mass spectrometry data processing system shown in FIG. 8 is hereinafter described.

1. The analysis parameters set in the user parameter input section 50 are temporarily stored in the analyzing procedure determining section 45. A measurement is subsequently started, and $MS^n$ measurements are continued until a suitable fragment ion is observed in a spectrum with respect to one of the ions observed in $MS^1$ measurement.
2. When the liquid or gaseous analyte separated by the chromatograph or the electrophoresis is introduced online into the mass spectrometer, the data including the retention time, and the solvent composition and the like is temporarily stored in the analyzing procedure determining section 45.
3. A mass spectrum data is transferred from the mass spectrum detector 32 to the ion charge z/mass m determining section 44. The ion charge z/mass m determining section 44 calculates the z and m of each peak to add them to the mass spectrum data. These data are temporarily stored in the analyzing procedure determining section 45.
4. The retention time and the mass spectrometry spectrum data are written in from the analyzing procedure determining section 45 to the measurement data storage section 43 as a set of information.
5. The data of the known oligosaccharide is required from the known oligosaccharide data base storing section 42. When specifying the use of the information on the retention time while searching data base, the data of the known oligosaccharide which is known to appear within the range of the retention time including acceptable variables is required.
6. The analyzing procedure determining section 45 temporarily obtains the data of the known oligosaccharide from the known oligosaccharide data base 42.
7. The mass spectrometry spectrum data and the spectrum data of the known oligosaccharide are transferred from the analyzing procedure determining section 45 to the spectrum matching processor 46.
8. The spectrum matching judgment results are transferred from the spectrum matching processor 46 to the analyzing procedure determining section 45.
9. When the spectrum matching judgment result is A (judged to be a known oligosaccharide) with judgment accuracy at a certain level or higher (A-1), identification information is added to the mass spectrometry spectrum data. A real time analysis is then terminated with respect to the ion.
10. When the spectrum matching judgment result is A (judged to be a known oligosaccharide) with judgment accuracy at a certain level or lower (A-2), the mass spectrometry spectrum data is transferred to the fragment ion combination reading processor 47 in order to perform $MS^{n+1}$ measurement to obtain the further information. The step to be taken is then advanced to the item 13.
11. When the spectrum matching judgment result is B (judged there is no corresponding known oligosaccharide) with judgment accuracy at a certain level or higher (B-1), the information saying it is an unknown oligosaccharide is added to the mass spectrometry spectrum data. The real time analysis is here terminated with respect to the ion.
12. When the spectrum matching judgment result is B (judged there is no corresponding known oligosaccharide) with judgment accuracy at a certain level or lower (B-2), the mass spectrometry spectrum data is transferred to the fragment ion combination reading processor 47 in order to perform $MS^{n+1}$ measurement to obtain further information. The step to be taken is then advanced to the item 13.
13. A fragment ion combination reading result is transferred to the optimum parent ion/CID condition determining section. When the optimum parent ion is available, the step to be taken is then advanced to the item 17.
14. When being judged an optimum parent ion is not found, the real time analysis is here terminated with respect to the ion.
15. When the spectrum matching result is C (mixture), a spectrum matching is again performed in the spectrum matching processor 46 on the assumption of a mixture of two kinds of oligosaccharides.
16. A judgment result is transferred to the analyzing procedure determining section 45. The step to be taken is advanced to the item 9.
17. The priorities of the combinations of $MS^{n+1}$ parent ion and the list of the optimum CID conditions with respect to each candidate ion are transferred from the optimum parent ion/CID condition determining section 48 to the analyzing procedure determining section 45.
18. With respect to the first one of the ions having the first priority, the CID conditions are transferred to the CID controller 33.
19. With respect to the first one of the ions having the first priority, an $MS^{n+1}$ measurement is performed in the mass analyzer 31.
20. The analyzing procedure determining section 45 obtains information on the retention time from the retention time measuring section.
21. The $MS^{n+1}$ spectrum data is transferred from the mass spectrum detector 32 to the ion charge z/mass m determining section 44. The ion charge z/mass m determining section 44 calculates the z and m of each peak to add them to the mass spectrum data. These data are temporarily stored in the analyzing procedure determining section.
22. The information on the retention time and $MS^{n+1}$ spectrum data are transferred from the analyzing procedure determining section 45 to the measurement data storage section 43.

With respect to the second and third ions of the fragment ion combination having the first priority, the same operations as those in the items 18 through 22 are hereinafter performed.

The analyzing procedure above makes it possible to efficiently perform a matching between an observed ion and a known substance, a judgment whether it is necessary to obtain further data or not, and a selection of a parent ion for obtaining further data.

An example of analysis is described below where a fragment ion formed by the desorption of a monosaccharide is observed in the mass spectrometry of oligosaccharide shown in FIGS. 9 and 10.

If the substance to be measured is oligosaccharide, ions formed by the one-by-one desorption of the saccharide from the terminal of the oligosaccharide are sometimes continuously observed in the $MS^n$ measurement.

Figure 9:
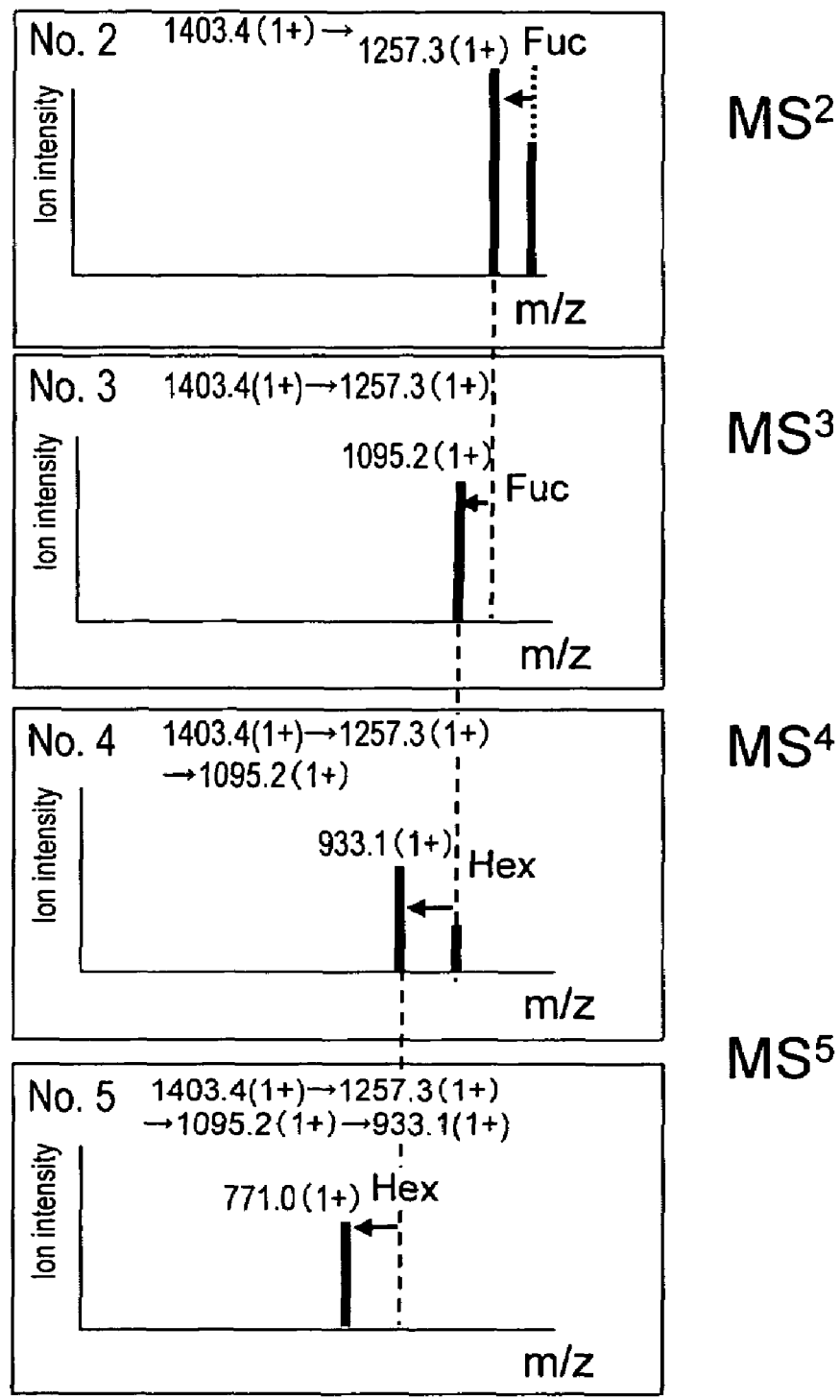
FIG. 9 is a schematic view showing mass spectra when a desorption of monosaccharide occurs.

FIG. 9 shows an example where a monosaccharide is one-by-one desorbed. The spectrum No. 2 in FIG. 9 is an $MS^2$ spectrum which is obtained using a univalent ion having an m/z of 1403.4 as a parent ion. A univalent ion having an m/z of 1257.3 is observed as well as the univalent parent ion having the m/z of 1403.4 which has not been fragmented. From the difference in mass calculated from two peaks, it is known that the univalent ion having an m/z of 1257.3 is the result of desorption of one fucose monosaccharide from a univalent ion having an m/z of 1403.4. This is shown using Fuc in FIG. 9. The spectrum No. 3 is an $MS^3$ spectrum which is obtained using a univalent ion having an m/z of 1257.3 as a parent ion. Observed here is a univalent ion having an m/z of 1095.2 formed by further desorption of one fucose. The spectrum No. 4 is an $MS^4$ spectrum obtained using a univalent ion having an m/z of 1095.2 as a parent ion. Observed here is a univalent ion having an m/z of 933.1 which is formed by further desorption of hexose. This is indicated with Hex in FIG. 9. The spectrum No. 5 is an $MS^5$ spectrum which is obtained using a univalent ion having an m/z of 933.1 as a parent ion. Observed here is a univalent ion having an m/z of 771.0 which is formed by further desorption of another hexose.

Desorption of monosaccharide causes little reduction in ion intensity. The $MS^n$ measurement can be repeated until a suitable fragment ion is observed. The desorbed substance can be judged to be a monosaccharide, from the difference in mass between the parent and product ions. Fucose, hexose, hexosamine, N-acetylhexosamine, sialic acid, and pentose are distinguishable because they have masses different from one another.

Figure 10:
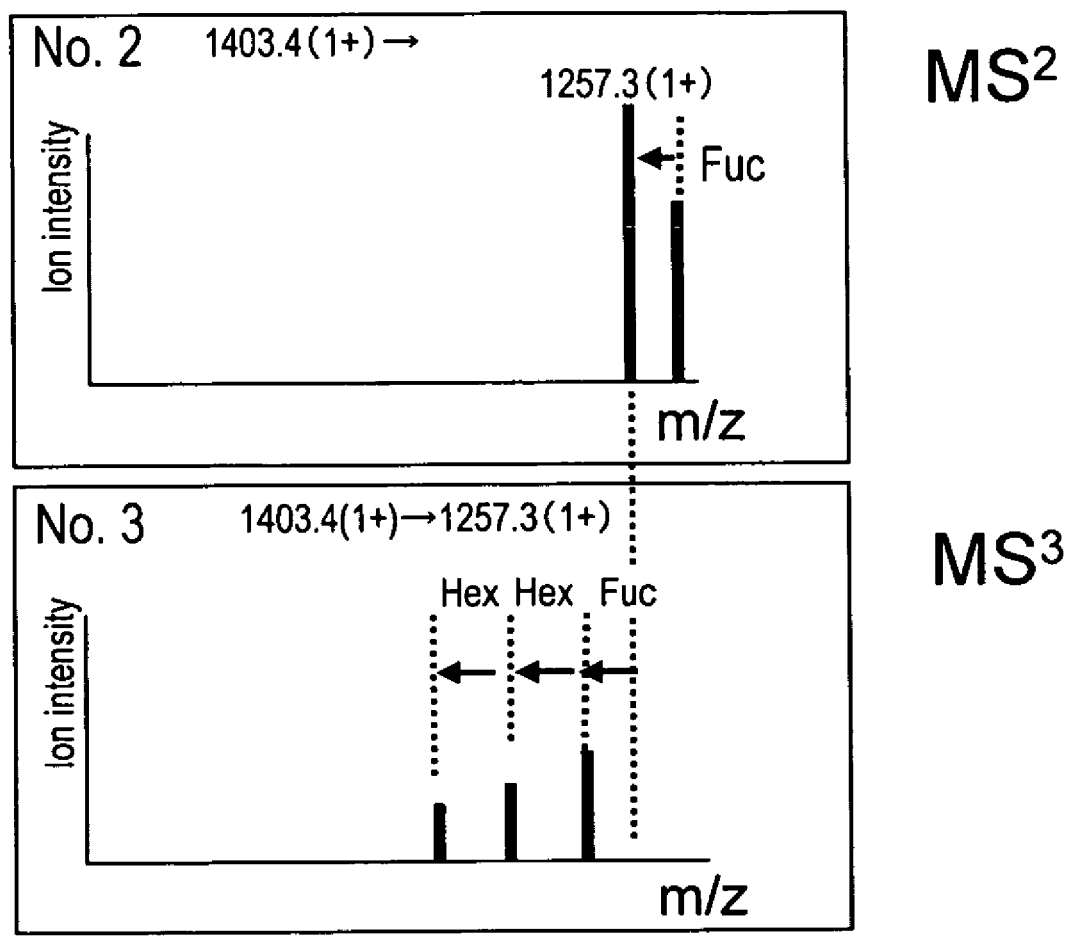
FIG. 10 is a schematic view showing mass spectra when a desorption of monosaccharide occurs.

FIG. 10 shows an example where oligosaccharide which has been subjected to the desorption of one, two, three, and so on of monosaccharides are simultaneously observed. The spectrum No. 2 in FIG. 10 is the $MS^2$ spectrum obtained using a univalent ion having an m/z of 1403.4 as a parent ion. A univalent ion having an m/z of 1257.3 is observed as well as the univalent parent ion having the m/z of 1403.4 which has not been fragmented. The univalent ion having the m/z of 1257.3 is known to be the one formed by desorption of one fucose monosaccharide from the univalent ion having the m/z of 1403.4 from the difference in mass between ions, which is calculated from two peaks. This is indicated using Fuc in FIG. 10. The spectrum No. 3 is an $MS^3$ spectrum which is obtained using a univalent ion having an m/z of 1257.3 as a parent ion. Simultaneously observed here are an ion formed by further desorption of one fucose, another ion formed by desorption of one fucose and one hexose, and the other ion formed by desorption of one fucose and two hexose.

However, oligosaccharide has a branched structure, and allows one-by-one reading of saccharides started from the terminal but does not provide information on the branched structure thereof. Therefore, it is necessary to obtain information for judgment by observing the ions (called ion a) formed by fragmenting ions having a branched structure left to dessociate a saccharide located at the root of the branch. The $MS^n$ measurements are repeated under CID conditions being adjusted until $MS^n$ spectrum in which such suitable fragment ions are observed. If a suitable fragment is observed, the $MS^n$ measurement is performed to identify or to obtain further information on the structure by means of spectrum matching and fragment combination reading.

The hexose has stereo isomers so as to produce many candidates of the structure of the oligosaccharide. Therefore, the structure of the oligosaccharide cannot be identified even if every saccharide can be read one-by-one starting from the terminal. Then, separation is performed using an LC by means of a separation column which takes a different retention time depending on the types of the stereo structure of the oligosaccharide. This method allows a plurality of oligosaccharides having the mass equal to one another but having different stereo structures to be narrowed down to a smaller number of candidates, thereby the efficiency of identification is improves.

Figure 11:
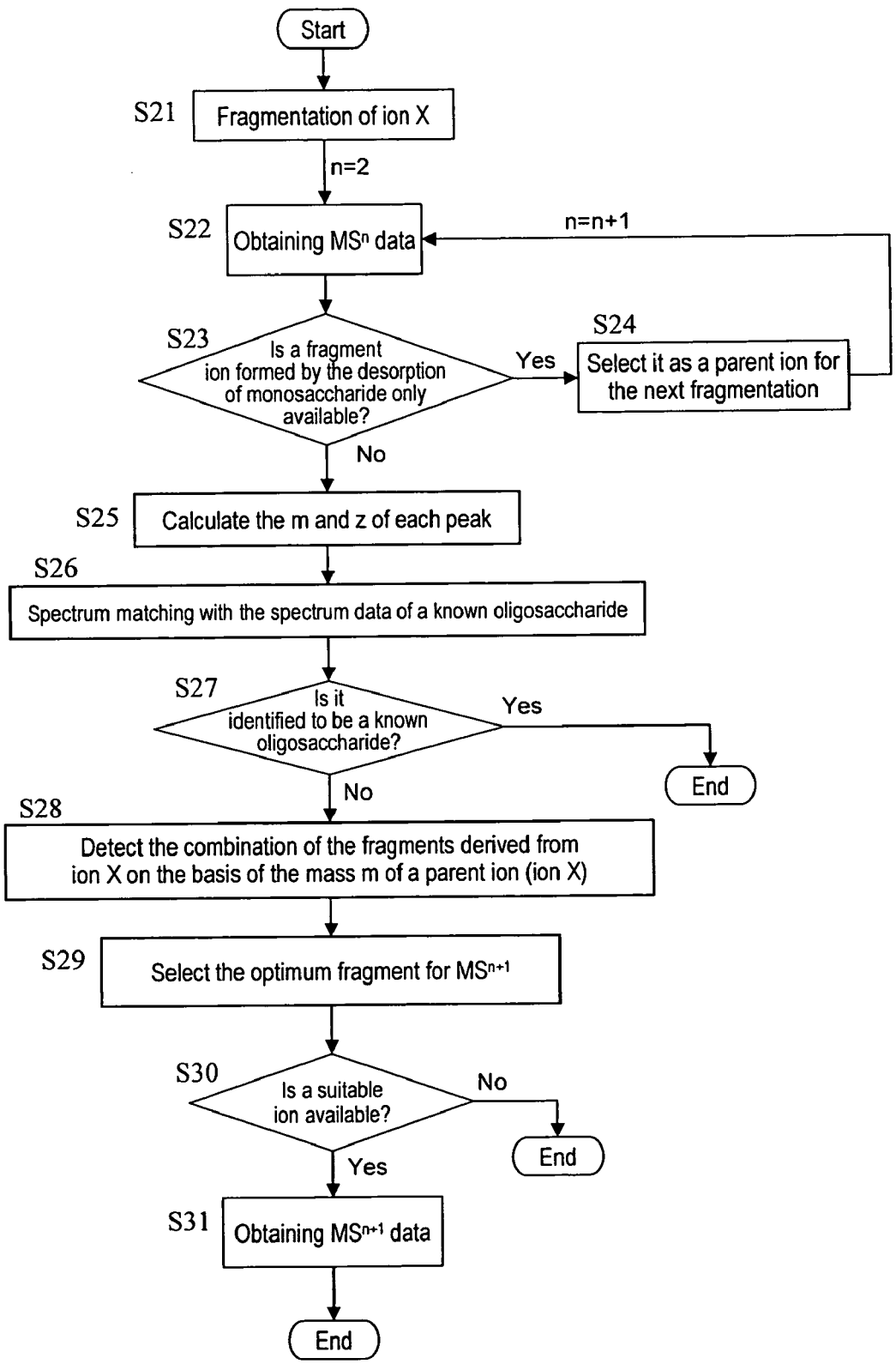
FIG. 11 is a flow diagram showing a real time analysis procedure to be performed when a desorption of monosaccharide occurs in the $MS^n$ measurement.

FIG. 11 shows an example of a real time analyzing procedure where a desorption of monosaccharide occurs. In the mass spectrometry system shown FIG. 1, analyzing is performed through the following procedure.

The $MS^2$ measurement is performed on an ion X having an m/z (S21, S22). When a mass spectrum of a case in which only the desorption of electrically neutral monosaccharides (neutral loss) occurs is mainly obtained, further fragmentations are performed to repeat the $MS^n$ measurement until a suitable fragment ion is observed (S23, S24). The z and m are calculated from the m/z value of the parent ion and intervals between the peaks of the isotopes (S25). When separation is performed by means of the liquid chromatography at a stage prior to the mass spectrometry, candidates of a known substance are narrowed down according to the information on the retention time. A known substance ion having a m vale which accords with that of the fragment ion is then searched to perform a spectrum matching between the $MS^n$ spectrum of the known substance ion and $MS^n$ spectrum of the actually measured ion (s26). When the measured ion is identified to be a known substance through the spectrum matching, the analyzing procedure is terminated with respect to this parent ion (S27, Yes).

When the measured ion is not identified to be a known substance through the spectrum matching (S27, No), the combination of the fragments derived from the parent ion is detected on the basis of the m value (S28) to select the optimum fragment as the parent ion for an $MS^{n+1}$ measurement (S29). If the number of fragments is specified to be 2, the optimum fragment ion as the parent ion for an $MS^{n+1}$ measurement is consequently selected on the basis of the equation (3) or (4) above. If a suitable combination of fragments is not available, the analysis is terminated (S30, No). If a suitable combination of fragments is available (S30, Yes), $MS^{n+1}$ measurement is performed using each fragment ion included in the combination as the parent ion (S31).

Figure 12:
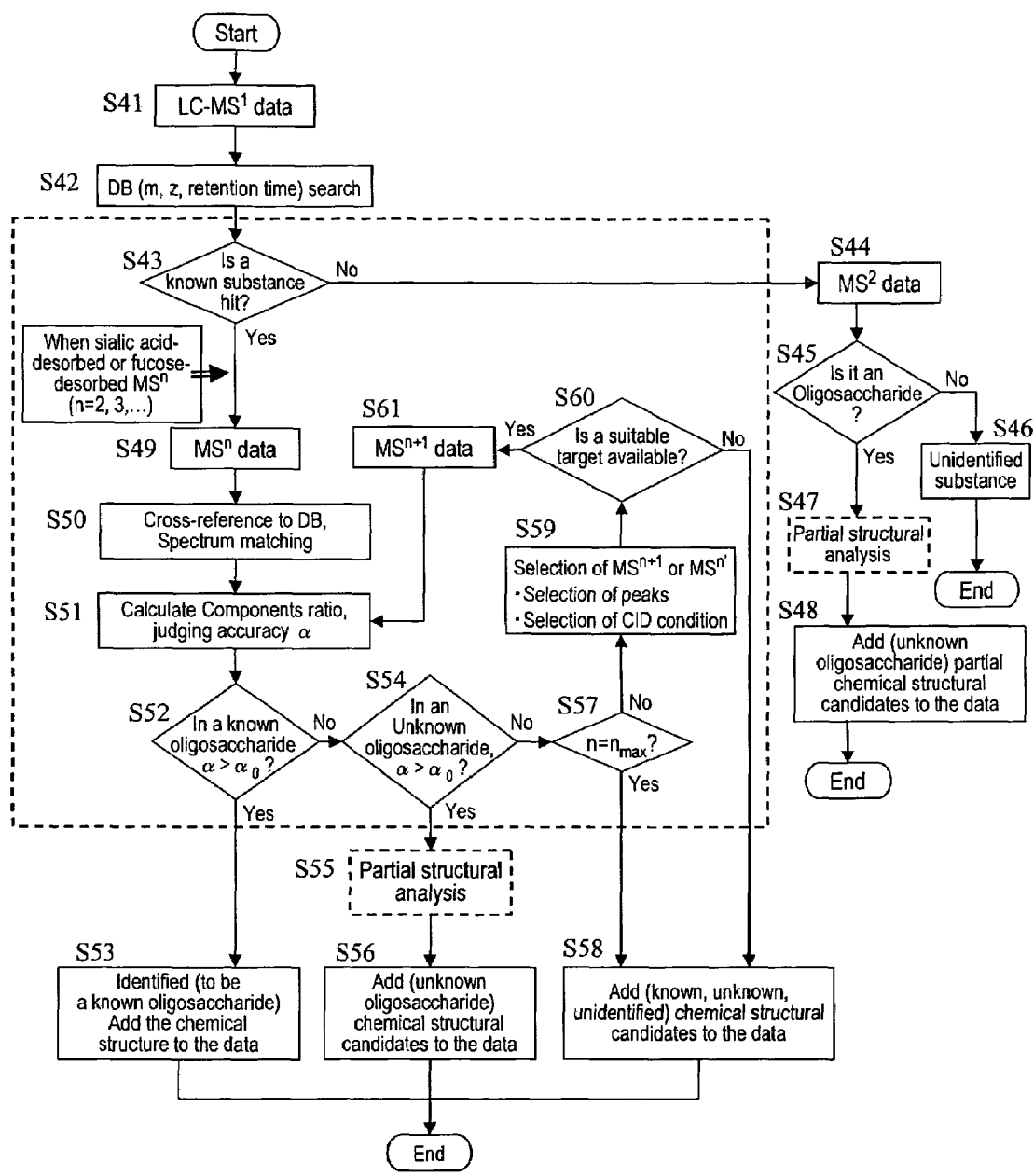
FIG. 12 is a flow diagram showing a real time measurement procedure in performing an $LC/MS^n$ analysis for multiple kinds of oligosaccharide mixtures.

FIG. 12 shows an example of a real time analyzing procedure where a mixed analyte of a known oligosaccharide and an unknown oligosaccharide is measured. This measurement targets the identification of the known oligosaccharide contained in the analyte. In FIG. 12, it is assumed that operations included in the expression of "partial analysis of structure" are the same as those surrounded by a dashed line. The analyzing procedure used in the mass spectrometry data processing system is described below.

First, $MS^1$ spectrum data is obtained (S41). The m and z values of the ions observed here are calculated. A known oligosaccharide which accords with the ion observed in the $MS^1$ spectrum is then searched according to the parameters previously specified by a user, for example m, z values, and retention time (S42).

The user can previously specify whether a further analysis is to be performed or not, when the result of search shows that accordance with the known oligosaccharide is not obtained (S43, No). When the user specifies a further analysis, the $MS^2$ measurement is performed (S44) to judge (S45) whether the observed ion is an impurity other than an oligosaccharide by making sure whether a fragment peak characteristic of an oligosaccharide appears or not. When judged to be an impurity, this judgment is written in the data storage section to terminate the analysis (S46). When judged to be an oligosaccharide, it is likely to have the structure partially equivalent to that of a known oligosaccharide. Therefore, a known oligosaccharide data base is searched to detect the fragment ion observed during fragmentation of a known oligosaccharide among fragment ions observed. An ion having a suitable intensity and an m/z value is selected as a parent ion from the detected ions to perform an $MS^n$ measurement (S47). Then, the partial chemical structure candidates of the unknown oligosaccharides are added to the data to be stored to the data storage section to terminate the procedure (S48). However, the user is capable of previously selecting whether analysis of partial structure of the unknown oligosaccharide is performed or not.

When the observed ion is judged to accord with a known oligosaccharide in the step 43, the $MS^2$ measurement is performed using the ion observed in $MS^1$ measurement as a parent ion. When the peaks which are the result of desorption of monosaccharide such as sialic acid and fucose appear in the $MS^2$ spectra, further fragmentations of $MS^3$, $MS^4$, and so on are repeated to perform $MS^n$ measurement until ion peaks appear which are formed by breaking of intramolecular bindings instead of by desorption of monosaccharide (S49). The obtained mass spectrum is checked with the $MS^n$ spectrum data of a candidate known oligosaccharide to perform spectrum matching (S50). When the spectrum is judged to contain one or more components, a further spectrum matching is performed on the assumption of multi components to calculate a component ratio. The accuracy of measurement is also calculated (S51).

When the fragment ion is judged to be of a known oligosaccharide with a certain accuracy or higher (S52, Yes), information that the fragment is identified to be a known oligosaccharide is added to the data to terminate the procedure (S53). When the fragment is judged to be an unknown oligosaccharide with a certain accuracy or higher (S54, Yes), the fragment is likely to have a structure partially equivalent to a known oligosaccharide. Therefore, the known oligosaccharide data base is searched to detect the fragment ions which have been observed in fragmentation of the known oligosaccharides among the observed fragment ions. The ions having a suitable ion intensity and an m/z value are selected from these ions to be used as a parent ion to perform $MS^n$ measurement (S55). After that, the candidates of the chemical structure of the unknown oligosaccharide are added to the data which is stored in the data storage section to terminate the procedure (S56). The user is capable of previously selecting whether the partial analysis of the structure of the unknown oligosaccharide is to be performed or not.

When the fragment is judged to be a known or unknown oligosaccharide with a certain accuracy or lower, a combination of ions that is suitable as a parent ion for the next $MS^{n+1}$ measurement is detected through a real time analyzing procedure (S59). When no suitable ions are available here, the procedure is terminated (S60, S58). When a suitable ion is found, the $MS^{n+1}$ measurement is performed to obtain a further fragment spectrum (S60, S61). When the n value reaches the maximum value which is previously set by the user (S57, Yes), information that no identification is achieved is added to the data which is to be stored in the data storage section to terminate the procedure (S58).

The analyzing procedure above allows efficient identification of a known oligosaccharide from a mixture of known and unknown oligosaccharides.

FIG. 13 shows an example of the user parameter input section used in the mass spectrometry system for the analysis of oligosaccharides according to the present invention. The information that is input by the user in each item is described.

Selection of a Real Time Analysis:

Selected is whether or not a real time data analysis such as spectrum matching and fragment reading is performed. When OFF is selected, it is decided that as conventionally, the selection of a parent ion is made in order of decreasing ion intensity, and the conditions are set on another condition setting screen provided separately.

Selection of the Data Base to be Used:

A generally disclosed data base, a self-made data base, and the like are made selectable.

Oligosaccharide Terminal Modification:

Information on derivatization such as pyridylamidation of a reduced terminal is selected. In the case of derivatization specifically by the user, the mass is input. Glycopeptide is also made selectable.

Threshold of the Peak Intensity of a Parent Ion:

The minimum value of the ion intensity of the ion which is selected as a parent ion for an $MS^n$ measurement is specified.

Use of Information on Retention Time in Search of a Data Base:

When a liquid or gaseous analyte which is separated in the LC is introduced online into the mass spectrometer, selected is whether or not the information on the retention time of the substance is used as a searching condition. When using the liquid chromatography, a liquid transferring method is selected to be downloaded. When using the information on the retention time for separation, the acceptable value of the variable of the retention time is set to perform identification by a spectrum matching on the known oligosaccharide having a retention time within the range of the set retention time.

Range of the m/z Value of the Parent Ion for $MS^n$ Measurement:

The range of the m/z value of the ion which is selected as a parent ion for $MS^n$ measurement is set. When the ion to be $MS^n$ measured or the ion not to be $MS^n$ measured is definite, the information can be previously input.

Spectrum Matching:

Selected is whether or not a judgment is performed by means of the spectrum matching prior to a fragment ion combination reading.

Fragment Ion Combination Reading:

Selected is whether or not fragment ion combination reading is performed. Also specified is whether or not the combination that constructs the parent ion is detected by combining several ions exclusive of desorbed ions. For example, when a checkbox 3 is checked, the combination of three ions a, b and c which meet the following equation is detected among the spectrum.

$$m = m_a + m_b + m_c + A$$

where: m is the mass of the parent ion; $m_a$ is the mass of the fragment ion a; $m_b$ is the mass of fragment ion b; $m_c$ is the mass of the fragment ion c; and A is the sum of the masses of the desorbed substances. Selected is whether or not the read information is stored along with the measured information.

Fragment Reading and MS" Measurement of an Unknown Oligosaccharide:

Selected is whether or not a fragment ion combination reading and an MS" measurement are performed on a substance which has been judged to be an unknown oligosaccharide by a spectrum matching.

Repetition of MS" Measurement with Respect to Ions Having a Low Ion-Intensity:

Selected is whether or not MS" measurement is repeatedly performed with ions having a low ion intensity used as a parent ion. An S/N value can be improved by repeated measurements and summation thereof. The maximum value of the ion intensity of the parent ion to be repeatedly measured is set. The maximum number of times of summation is specified.

Through procedure above, the user is capable of setting a real time analysis as necessary.

The examples of the items of the information on the measurement data to be stored in the measurement data storage section are described. The measurement data includes a spectrum number, measuring conditions (positive/negative ion mode, ion in-take time, CID energy, and the like), the list of the m/z and ion intensity I (m/z) of the ions which are observed in the spectrum, and the m/z value of the parent ion in each MS" measurement ($n \geq 2$). When the judgment of z and calculation of m are performed by intervals between the peaks of the isotopes, the information is also added. The information on the code number of the corresponding known substance and the accuracy used in judgment is added with respect to the ion of the substance which is judged to be a known substance by spectrum matching. The information on the fact that it is an unknown substance, to which a symbol is given, and on the accuracy used in the judgment is added with respect to the ion of the substance which is judged to be an unknown substance by spectrum matching.

FIG. 14 shows an example of the measurement data to be stored which is obtained by performing the fragment ion combination reading process. A list of combinations of the fragment ions which are judged, for every spectrum, to be a combination is recorded along with the information on desorbed ions.

Among items above, essential items are a spectrum number, the m/z value of the parent ion, the list of the m/z and the ion intensity I (m/z) of the ions observed in the spectrum. The user is capable of setting whether or not other items are stored, taking into consideration the volume of data and the speed at which post-processing is performed. Alternatively, it is specified that they are stored in a separate file to be referred to as necessary.

Figure 15:
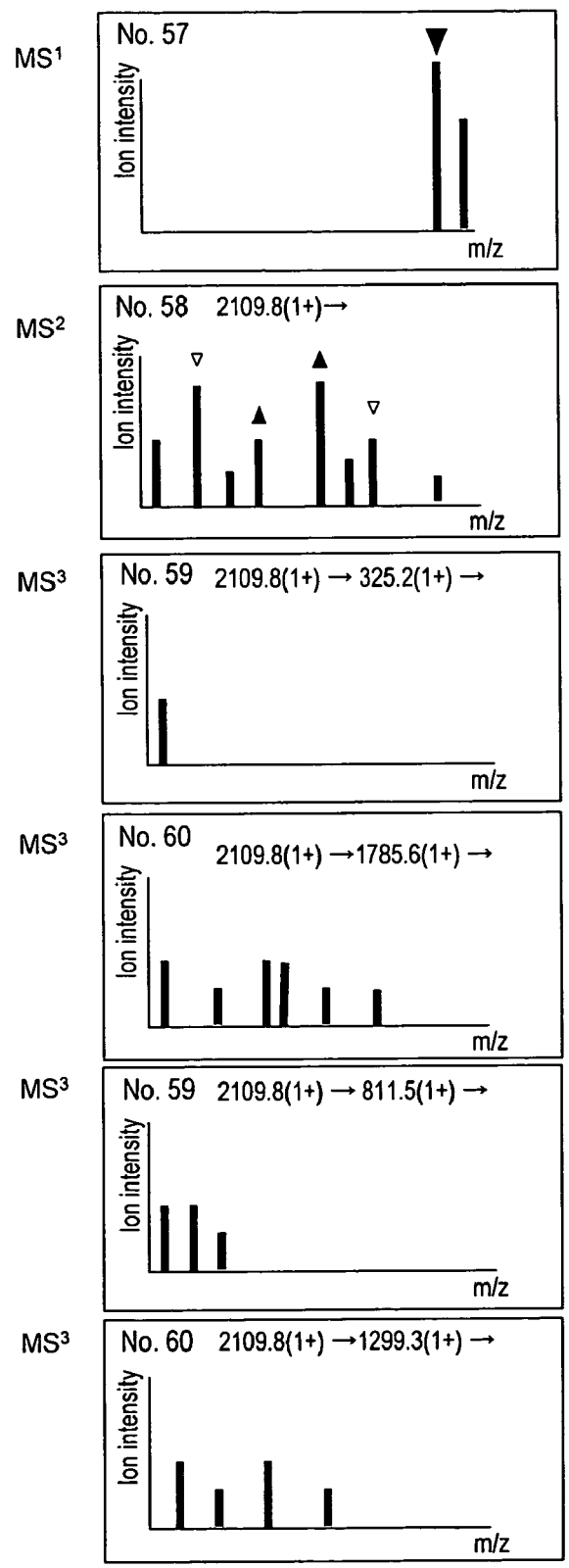
FIG. 15 shows examples of displays representing data which a user confirms after measurement with respect to the measurement data obtained from a real time fragment combination reading processing
Figure 16:
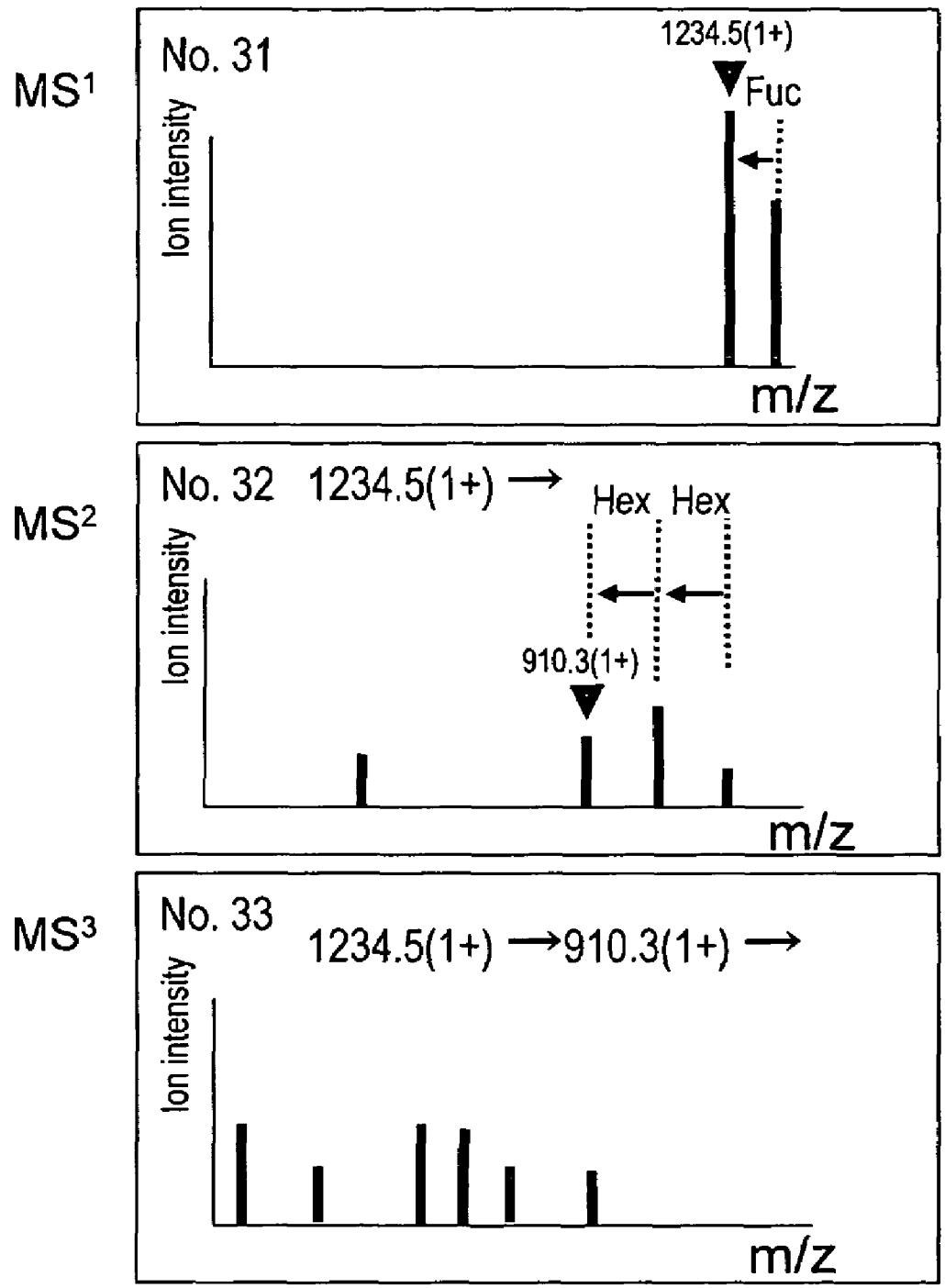
FIG. 16 shows examples of a display representing data which a user confirms after measurement with respect to the measurement data obtained from a real time monosaccharide desorption reading processing.

FIGS. 15 and 16 show an example of the method for displaying the information on the spectrum which is to be displayed on a screen when the user checks the measured data during or after the measurement.

FIG. 15 shows the mass spectra Nos. 57 to 62 among the spectra obtained by means of a mass spectrometer and numbered in chronological order, for example, No. 1, No. 2, and so on. The spectrum number may be displayed in terms of retention time. The m/z and z of the parent ions are displayed when MS" measurement is performed. When a subsequent MS"+1 measurement is performed, the peak which becomes the parent ion is marked. For example, spectrum No. 58 in FIG. 15 is the spectrum of MS² measurement which is performed using one of the ions which have been observed in spectrum No. 57 as a parent ion. The peak in spectrum No. 57, which has become the parent ion, is thus marked by, for example, ▼ shown in FIG. 15. When the fragment ion combination reading is performed to perform MS"+1 measurement using a plurality of fragment ions contained in the obtained combinations as the parent ions, each combination is displayed with a mark different in color or in shape. For example, with respect to spectrum No. 58 in FIG. 15, a real time analysis of fragment ion reading is performed. As a result, a total of two pairs of ions, which include a pair of ions shown with ◇, and a pair of ions shown with ▲, are detected as a combination which constructs the original ions. Four MS³ spectra No. 59 to No. 62 are obtained using these four ions as each parent ion.

When reading of the desorption of monosaccharide is performed, the kinds of the desorbed saccharides are shown as in FIG. 16. For example, two kinds of ions are observed in spectrum No. 31 in FIG. 16, and have a difference in mass between them which is equal to the mass of one fucose. Thus, Fuc is displayed between their peaks. When MS² spectrum is obtained using a univalent ion having an m/z of 1234.5, which is an ion having the lower mass, as a parent ion, a mark ▼ is placed above the univalent ion having the m/z of 1234.5. Spectrum No. 32 is an MS² spectrum obtained using a univalent ion having the m/z of 1234.5 as a parent ion. Here, a one-hexose desorption resultant ion and a two-hexose desorption resultant ion are detected because of the differences in mass between the parent ion and the product ions. Thus, Hex is each displayed between these peaks. Also, when MS³ spectrum is obtained using a univalent ion having an m/z of 910.3, which is the two-hexose desorption resultant ion, as a parent ion, a mark ▼ is placed above the univalent ion having the m/z of 910.3.

The displaying method above allows users to be able to read the real time processing at one view after the measurement.

Figure 17:
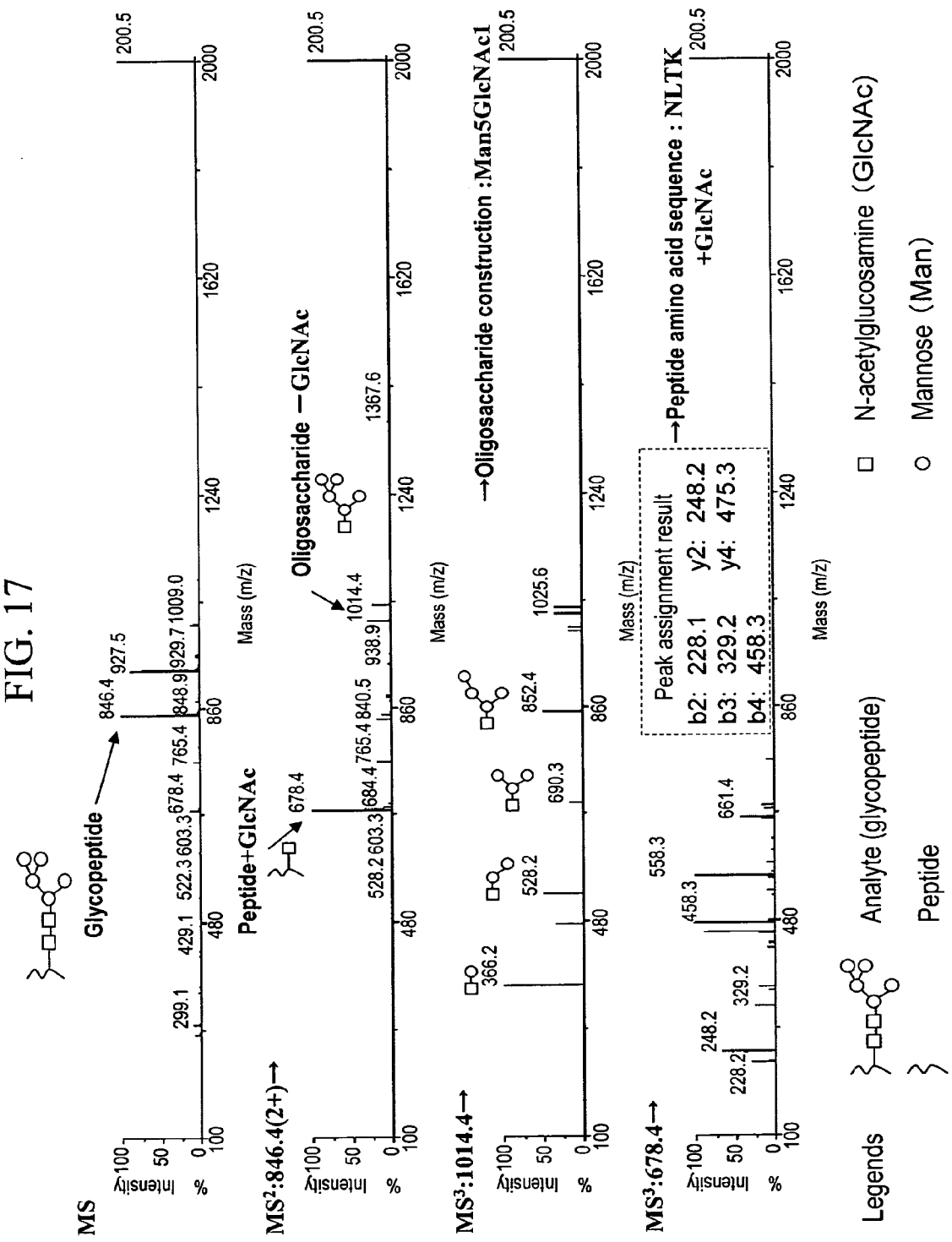
FIG. 17 shows $MS^3$ spectra obtained by applying fragment ion reading processing to a $MS^2$ spectrum measured by use of an oligosaccharide as an analyte.

FIG. 17 shows an example of the MS" measurement of glycopeptide according to the present invention. The analyte is glycopeptide having a mass of 1690.8, which is formed by binding peptide asparagine N having an amino acid sequence NLTK with oligosaccharide composed of two N-acetylglucosamines and five mannoses.

In the MS spectrum, a bivalent ion which is an adduct of glycopeptide with two protons is observed at m/z 846.4 (m/z= (1690.8+1.0×2)÷2=846.4). Then, an MS² measurement is performed using the bivalent ion of glycopeptide as the parent ion. A two-fragment combination reading process is performed with respect to the MS² spectrum. As a result, a univalent ion having m/z 1014.4 and a univalent ion having m/z 678.4 are detected as a fragment combination. That is to say, when calculation exclusive of the added protons is performed, the result shows that the mass accords with that of the parent ion without any ion desorbed as indicated in the equation below.

(1014.4−1.0)+(678.4−1.0)=1690.8

MS³ measurements are then performed using, as the parent ion, a ion having an m/z 1014.4 and another ion having an m/z 678.4, respectively which are observed in the MS² spectra. Analysis of an MS³ spectrum which is obtained using an ion having m/z 1014.4 as a parent ion results in observation of univalent ions having an m/z 852.4, another m/z 690.3, still another m/z 528.2, and yet another m/z 366.2. The differences in mass between the parent ion and these peaks are as follows.

1014.4−852.4=162.0

852.4−690.3=162.1

690.3−528.2=162.1

528.2−366.2=162.0

The calculation results approximately accord with 162.05 of the mass of one mannose to be desorbed within the margin of measurement error. Also, m/z 366.2 accords with 366.23 of the mass of adduct of the combined molecule of N-acetylglucosamine, which is the typical core structure of oligosaccharide, and mannose with a proton within the margin of measurement error. Therefore, the parent ion having m/z 1014.4 is identified to be oligosaccharide which is a combined molecule of ManGlcNAc structure which is a combined molecule of N-acetylglucosamine, which is the typical core structure of oligosaccharide, and mannose, and further four mannoses.

Analysis of $MS^3$ spectra obtained using the ion having an m/z 678.4 as the parent ion results in observation of the peaks of univalent ions having m/zs 475.3, 458.3, 329.2, 248.2, and 228.1 respectively. This observation suggests that the ion is identified to be a peptide having an amino sequence NLTK. A 203.1 difference, between 474.3 of the mass of peptide having the amino acid sequence NLTK exclusive of a proton and 677.4 of the mass of the parent ion exclusive of a proton, accords with 203.07 of the mass of one GlcNAc to be desorbed within the margin of measurement error.

Thus, the bivalent ion having an m/z 846.4 observed in $MS^1$ spectrum is identified to be a combined molecule of peptide having the amino acid sequence NLTK and oligosaccharide composed of five mannoses, two N-acethylglucosamines. FIG. 17 shows the structure of the analyte and the assignment of the observed peaks.

Fragment ion combination reading process is performed as described above so that two minimum times of $MS^3$ measurements allow the oligosaccharide composition of glycopeptide and the amino acid sequence of peptide to be identified. This leads to a less time-requiring and more reliable identification.

What is claimed is:

1. A mass spectrometry system, comprising:
a mass spectrometer which mass-analyzes an ionized analyte; and
an information processor,
wherein the mass spectrometer has a function of selectively fragmenting a parent ion having a particular m/z which appears in a mass spectrum and a function of mass-analyzing the fragment ions resulting from fragmentation of the parent ion,
wherein the information processor has a fragment ion combination processing section, which receives information on a parent ion and a plurality of fragment ions resulting from fragmentation of the parent ion, and which makes a combination of the fragment ions reconstructing the mass of the parent ion by adding masses of the fragment ions, and also has a function of instructing the mass spectrometer to fragment and mass-analyze the fragment ions contained in the combination of the fragment ions, and
wherein the fragment ion combination processing section makes the combination of the fragment ions, which meets the following equation (1):

$$m=m_1+m_2+\ldots+m_s+A \text{ (s is a positive integer not less than 2 and less than } n) \quad (1)$$

where: m is a mass of the parent ion; $m_1, m_2, \ldots, m_n$ (n is a number of the fragment ions and not less than 2) are masses of the plurality of fragment ions; and A is a mass of a molecule dissociated from the parent ion with no electric charge during a fragmentation of the parent ion.

2. The mass spectrometry system according to claim 1, wherein the information processor instructs the mass spectrometer to fragment and mass analyze the fragment ions contained in the combination of the fragment ions in order of ion intensity when the fragment ion combination processing section has made a plurality of the combinations of the fragment ions.

3. The mass spectrometry system according to claim 1, further comprising:
a chromatograph which separates an analyte into substances; and
an ion source which ionizes the analyte separated by the chromatograph, and
wherein the mass spectrometer mass-analyzes the analyte which has been ionized by the ion source.

4. A mass spectrometry method comprising:
a process of ionizing an analyte;
a process of mass-analyzing the ionized analyte;
a first fragmentation process of fragmenting a parent ion selected from ions observed in a mass spectrometry;
a process of mass-analyzing a plurality of fragment ions generated through the first fragmentation process;
a process of making a combination of the fragment ions reconstructing the mass of the parent ion by adding the masses of the fragment ions using a result of the mass spectrometry;
a second fragmentation process of fragmenting the fragment ions contained in the combination of the fragment ions; and
a process of mass-analyzing the fragment ions generated through the second fragmentation process;
wherein the combination of fragment ions, which meets the following equation (2), is made:

$$m=m_1+m_2+\ldots+m_s+A \text{ (s is a positive integer not less than 2 and less than } n) \quad (2)$$

where: m is a mass of the parent ion; $m_1, m_2, \ldots, m_n$ (n is a number of the fragment ions and not less than 2) are masses of the plurality of fragment ions generated through the first fragmentation process; and A is a mass of a molecule dissociated from the parent ion with no electric charge during the first fragmentation process.

5. The mass analyzing method according to claim 4, wherein the fragment ions contained in the combination of the fragment ions are fragmented through the second fragmentation process in order of ion intensity when the plurality of the combinations of the fragment ions, which meet the equation (2) is available.

6. The mass analyzing method according to claim 4, wherein the analyte is one separated by chromatograph.

7. A program for instructing a computer to execute a process of making a combination of fragment ions which reconstruct the mass of the parent ion with information, received from the mass spectrometer, on the parent ion and the plurality of fragment ions generated through the fragmentation of the parent ion, and a process of instructing a mass spectrometer to fragment and mass-analyze the fragment ions contained in the combination of the fragment ions,
wherein a combination of the fragment ions which meets the following equation (3) is made:

$$m=m_1+m_2+\ldots+m_s+A \text{ (s is a positive integer not less than 2 and less than } n) \quad (3)$$

where: m is a mass of the parent ion; $m_1, m_2, \ldots, m_n$ (n is a number of the fragment ions and not less than 2) are masses of the plurality of fragment ions; and A is a mass of a molecule dissociated from the parent ion with no electric charge during fragmentation of the parent ion.

* * * * *